(12) United States Patent
Menschik et al.

(10) Patent No.: US 8,615,412 B2
(45) Date of Patent: *Dec. 24, 2013

(54) METHODS AND SYSTEMS FOR MANAGING DISTRIBUTED DIGITAL MEDICAL DATA

(75) Inventors: Elliot D. Menschik, Morris Plains, NJ (US); Christopher R. Corio, Seattle, WA (US); Wayne F. Davis, Ocean City, NJ (US); Haig C. Didizian, Penn Valley, PA (US)

(73) Assignee: MEDecision, Inc., Wayne, PA (US)

( * ) Notice: Subject to any disclaimer, the term of this patent is extended or adjusted under 35 U.S.C. 154(b) by 412 days.

This patent is subject to a terminal disclaimer.

(21) Appl. No.: 12/395,408

(22) Filed: Feb. 27, 2009

(65) Prior Publication Data

US 2009/0164255 A1 Jun. 25, 2009

Related U.S. Application Data

(62) Division of application No. 10/222,056, filed on Aug. 16, 2002, now Pat. No. 7,523,505.

(51) Int. Cl.
*G06Q 50/00* (2012.01)
*G06F 7/00* (2006.01)

(52) U.S. Cl.
USPC ..................................... 705/3; 707/4; 726/26

(58) Field of Classification Search
USPC ............................................................ 705/3
See application file for complete search history.

(56) References Cited

U.S. PATENT DOCUMENTS 5,469,353 A 11/1995 Pinsky
5,513,101 A 4/1996 Pinsky
5,655,084 A 8/1997 Pinsky
(Continued)

FOREIGN PATENT DOCUMENTS

WO WO 96/41288 12/1996
WO WO 00/65522 11/2000

OTHER PUBLICATIONS

"Guardian Angel—Personal Lifelong Active Medical Assistant", The MIT CDM Guardian Angel Project, Last Modified Mar. 15, 2002, http://groups.csail.mit.edu/medg/projects/, Downloaded from Internet Apr. 14, 2008, 9 pages.

(Continued)

*Primary Examiner* — Hiep V Nguyen
(74) *Attorney, Agent, or Firm* — Woodcock Washburn LLP

(57) ABSTRACT

A network for mediating the peer-to-peer transfer of digital patient medical data includes a plurality of distributed agents each associated with a health care provider and connected to a central system. Periodically the agents collect local information relating to patient medical files and/or data streams, for example diagnostic images and associated reports, and process that information into metadata files acting as pointers to the original files. The metadata files are transmitted to the central system where they are parsed and the attributes are stored on the central system in patient records with records from the same patient grouped together whenever possible. Registered users can search the central system, even in the absence of a unique identifier, to identify patient records pointing to the remote patient medical files. Upon finding a patient medical file, the invention provides a streamlined process for communicating access authorization from the patient to the hospital or facility storing the medical files. Once patient authorization is received, secure processes are provided for transferring the data in its entirety to or for viewing by the user in a peer-to-peer fashion.

16 Claims, 24 Drawing Sheets

(56) References Cited

U.S. PATENT DOCUMENTS

| | | | |
|---|---|---|---|
| 5,724,575 | A | 3/1998 | Hoover et al. |
| 5,845,255 | A | 12/1998 | Mayaud |
| 5,862,325 | A * | 1/1999 | Reed et al. ............... 709/201 |
| 5,867,821 | A | 2/1999 | Ballantyne et al. |
| 5,924,074 | A | 7/1999 | Evans |
| 5,995,939 | A | 11/1999 | Berman et al. |
| 6,012,035 | A | 1/2000 | Freeman et al. |
| 6,083,248 | A | 7/2000 | Thompson |
| 6,678,703 | B2 | 1/2004 | Rothschild et al. |
| 6,804,787 | B2 | 10/2004 | Dick |
| 6,988,075 | B1 | 1/2006 | Hacker |
| 7,234,064 | B2 | 6/2007 | Menschik et al. |
| 7,523,505 | B2 | 4/2009 | Menschik et al. |
| 2001/0029322 | A1 | 10/2001 | Iliff |
| 2002/0010679 | A1 | 1/2002 | Felsher |
| 2002/0029157 | A1 | 3/2002 | Marchosky |
| 2002/0103811 | A1 * | 8/2002 | Fankhauser et al. ....... 707/104.1 |
| 2003/0158753 | A1 | 8/2003 | Bernston et al. |
| 2004/0034550 | A1 | 2/2004 | Menschik et al. |
| 2005/0027995 | A1 | 2/2005 | Menschik et al. |

OTHER PUBLICATIONS

Abbett, "Subscription Architecture", OpenIndivo Documentation Wiki, http://wiki.indivohealth.org/index, Last Modified Sep. 14, 2007, 5 pages.
Archives: "High-Technology Medical Awards Announced", National Library of Medicine Supports 24 Next Generation Internet Projects, www.nlm.nih.gov, Oct. 14, 1998, 7 pages.
Channin et al., "Integrating the Healthcare Enterprise: A Primer, Part 3, What Does IHE Do for Me?", RadioGraphics, Sep.-Oct. 2001, 21(5), 1351-1358.
Channin et al., "Integrating the Healthcare Enterprise: A Primer, Part 5, The Future of IHE", RadioGraphics, Nov. 2001, 21, 1605-1608.
Channin, "Integrating the Healthcare Enterprise: A Primer. Part 2, Seven Brides for Seven Brothers: The IHE Integration Profiles", RadioGraphics, Sep. 2001, 21, 1343-1350.
Channin, "Is it Time for PACSter?", Journal of Digital Imaging, Jun. 2001, 14(2), 52-53.
Digital Imaging and Communications in Medicine (DICOM). NEMA Publications PS 3.1-PS 3.12. Rosslyn, VA: The National Electrical Manufacturers Association, Part 1: Intro & Overview, (no month available) 2001, 19 pages.
Eysenbach et al., "Evidenced-Based Patient Choice and Consumer Health Informatics in the Internet Age", J. Med Internet Res, Apr.-Jun. 2001, 3(2), 15 pages.
Henderson et al., "Integrating the Healthcare Enterprise: A Primer, Part 4, The Role of Existing Standards in IHE", RadioGraphics, Nov. 2001, 21, 1597-1603.
Hickman et al., "The SSL Protocol", Netscape Communications, Nov. 1995, 60 pages.
Katehakis et al., "Towards a Virtual Electronic Healthcare Record", The Patient Clinical Data Directory, Version 3.14, Dec. 18, 1998, 41 pages.
Kent et al., "IP Authentication Header", RFC 2402, Internet Engineering Task Force, Nov. 1998, 16 pages.
Kent et al., "IP Encapsulating Security Payload (ESP)", RFC 2406, Internet Engineering Task Force, Nov. 1998, 16 pages.
Kent et al., "Security Architecture for the Internet Protocol", RFC 2401, Internet Engineering Talk Force, Nov. 1998, 48 pages.
Kim et al., "Integrated Multimedia Medical Data Agent in E-Health", Pan-Sydney Area Workshop on Visual Information Processing (VIP2001), Sydney, Australia, Oct. 10, 2002, 5 pages.
Lee et al., "A Metadata Oriented Architecture for Building Datawarehouse", Journal of Database Management, Oct.-Dec. 2001, 12(4), 15-25.
Mandl et al., "BMC Medical Informatics and Decision Making", BMS Medical Informatics and Decision Making, www.biomedcentral.com, Sep. 12, 2007, 7, 10 pages.
Marks, "Implementing HIPAA—Guidelines for Initiating HIPAA Systems Implementing Projects", MONDAQ, Jul. 17, 2001, 20 pages.
Martinez et al., "Application of the OSF Distributed Computing Environment to Global PACS", Proc SPIE, 2165, Nov. 29, 1994, 509-518.
Martinez et al., "OSF Distributed Computing Environment for Multimedia Telemedicine Services in Global PACS", Proc SPIE, May 12, 1995, 220-231, 7 pages.
Martinez et al., "Remote Consultation and Diagnosis in a Global PACS Environment", Proc SPIE, Oct. 29, 1993, 296-307.
Martinez et al., "Synchronized Voice and Image Annotation in Remote Consultation and Diagnosis for the Global PACS", Proc SPIE, 2165, Nov. 29, 1994, 9-20.
Martinez, "Distributed System Software Via NSFNET for Global Picture Archiving and Communications Systems (Global PACS)", NSF Project NCR-9106155, University of Arizona, Part II, Summary of Completed Project, (no month available) 1991-1995, 16 pages.
Mavridis "Access Control Based on Attribute Certificates for Medical Intranet Applications", J. Med Internet REs, www.jmir.org/2001/1/e9, Jan.-Mar. 2001, 3(1), 13 pages.
Neame "Smart Cards—The Key to Trustworthy Health Information Systems", British Medical Journal (International (IBMJ), Feb. 22, 1997, 314(7080), 573-577.
NLM's Next Generation Internet (NGI) Awards, United States National Library of Medicine, National Institutes of Health, www.nlm.nih.gov/research/ngiinit.html, Last Updated Nov. 26, 2007, 2 pages.
Ooi et al., "Relational Data Sharing in Peer-Based Data Management Systems", Department of Computer Science, National University of Singapore, www.sigmod.org/sigmod/record/issues/0309/C11.ooibc.pdf, Sep. 2003, 32(3), 59-64.
Philipps, "What's in that Data Warehouse?", Records Management Quarterly, Apr. 1997, 31(2), 54-56.
Ribeiro et al., "CyclopsDistMedDB—A Transparent Gateway for Distributed Medical Data Access in DICOM Format", Computer-Based Medical Systems, (CBMS 2002) Proceedings of the 15th IEEE Symposium, Jun. 4-7, 2002, 315-320.
Riva et al., "The Personal Internetworked Notary and Guardian", International Journal of Medical Informatics, Jun. 2001, 62, 27-40.
Sakai, "Metadata for Evidence Based Medicine Resources", National Institute of Informatics, www.nii.ac.jp, Oct. 24-26, 2001, 81-85.
Siegel et al., "Integrating the Healthcare Enterprise: A Primer, Part 1, Introduction", RadioGraphics, Sep.-Oct. 2001, 21, 1339-1341.
Stanton, "A Holiday Gift from Health and Human Services: Final HIPAA Privacy Regulation Contain Significant Changes", MODAQ, Jul. 16, 2001, 10 pages.
Stojanovic et al., "A Framework for Knowledge Management on the Semantic Web", AIFB Institute, University of Karlsruhe, Germany, http://citeseer.ist.psu.edu, (no month available), 2002, 4 pages.
Szolovits et al., "Guardian Angel: Patient-Centered Health Information Systems", TR-604 MIT Laboratory for Computer Science, http://groups.csail.mit.edu/medg/projects/ga/manifesto, May 1994, 43 pages.
Wilson et al., "Filmless PACS in a Multiple Facility Environment", Proc SPIE, 2711, Feb. 13, 1996, 500-509.
Wilson et al., "Virtual PACS, Open Systems and the National Information Infrastructure", Proc SPIE, 2435, Sep. 28, 1995, 553-563.
Winkler et al., "Advanced Methods of Record Linkage", American Statistical Association, Proceedings of the Section of Survey Research Methods, (no month available) 1994, 467-472, 24 pages.
Winkler et al., "Matching and Record Linkage", In Business Survey Methods (ed. B.G. Cox), J. Wiley, NY, (no month available) 1995, 355-384, 38 pages.

* cited by examiner

FIG. 6A Prior Art

| PEOPLE_ID | TITLE | FIRST | MIDDLE | LAST_PRE | LAST | GEN | OCC1 | OCC2 |
|---|---|---|---|---|---|---|---|---|
| 1 | | JOHN | M | | HARLOW | | MD | |
| 2 | | PHINEAS | P | | GAGE | | | |
| 3 | SIR | WILLIAM | | | OSLER | | MD | |
| 4 | | WALTER | | | WHITMAN | | | |
| 5 | | JOHN | | VON | NEUMANN | | PHD | |
| 6 | KING | HENRY | | | WINDSOR | VIII | | |
| 7 | | HENRY | | | YANG AST | | MD | |
| 8 | | ELLIOT | D | | MENSCHIK | | MD | PHD |

FIG. 6B Prior Art

| ABBR_ID | NO | NAME | TYPE | WITHIN | WITHIN_ID | CITY | ST | POSTAL | COUNTRY |
|---|---|---|---|---|---|---|---|---|---|
| 1 | 10 | MAIN | ST | | | CAVENDISH | VT | 05142 | USA |
| 2 | 250 | ELM | AVE | APT | 205 | LUDLOW | VT | 05149 | USA |
| 3 | 3400 | SPRUCE | ST | SILVER | 1 | PHILADELPHIA | PA | 19104 | USA |
| 4 | 73 | DIRT | RD | | | BOND HEAD | ONT | | CAN |

| INST_ID | INSTITUTION NAME |
|---|---|
| 1 | THE JOHNS HOPKINS HOSPITAL |
| 2 | MASSACHUSETTS GENERAL HOSPITAL |
| 3 | HOSPITAL OF THE UNIVERSITY OF PENNSYLVANIA |
| 4 | CLINICAL PRACTICES OF THE UNIVERSITY OF PENNSYLVANIA |
| 5 | CHILDREN'S HOSPITAL OF PHILADELPHIA |
| 6 | CAVENDISH PHYSICIANS |

FIG. 6C Prior Art

| MEDICAL_RECORD_NUMBER | PEOPLE_ID | INST_ID |
|---|---|---|
| A1665C92 | 6 | 6 |
| GF29842810 | 4 | 3 |
| 050843732SDSH3 | 5 | 2 |

| STUDY _ID | INST _ID | PATIENT _ID | DATE | ACCESSION_NUM | STUDY_INSTANCE_UID | REFERRING_PHYSICIAN_ID |
|---|---|---|---|---|---|---|
| 1 | 6 | 2 | 18480913 | 987654321 | 1.3.46.670589.5.2.7.5524983643.1026922850.514802 | 1 |
| 2 | 3 | 4 | 20010901 | 123456789 | 1.3.46.670589.5.4.7.5584745612.9484720102.948267 | 3 |

| SERIES_ID | STUDY_ID | MODALITY | SERIES_INSTANCE_UID | BODY_PART | LATERALITY |
|---|---|---|---|---|---|
| 1 | 1 | MR | 1.3.46.670589.5.2.7.5524983643.1026922850.541636 | HEAD | |
| 2 | 1 | MR | 1.3.46.670589.5.2.7.5524983643.1026922850.541637 | HEAD | |
| 3 | 1 | MR | 1.3.46.670589.5.2.7.5524983643.1026922850.541638 | HEAD | |
| 4 | 2 | CR | 1.3.46.670589.5.4.7.5584745612.9484720102.948987 | CHEST | |
| 5 | 3 | CT | 1.3.46.670589.5.4.7.9812734124.8237374910.129734 | ADBDOMEN | |
| 6 | 4 | MR | 1.3.46.670589.5.4.7.8436129401.7492047121.926413 | KNEE | RIGHT |
| 7 | 5 | US | 1.3.46.670589.5.4.7.8392034793.7398203481.736120 | PELVIS | |
| 8 | 6 | NM | 1.3.46.670589.5.4.7.3513289312.7291038471.128459 | CHEST | |

196A 196B 196C 196D 196E 196F 196-1
196-2
196-3
196-4
196-5
196-6
196-7
196-8

| AUTH_ID | FORM_ID | PHYSICIAN_ID | PATIENT_ID | INST_ID | STUDY_ID | REQ_DATE | AUTH_DATE | SIGNATURE | STATUS |
|---|---|---|---|---|---|---|---|---|---|
| 1 | 3 | 1 | 2 | 6 | 1 | 20020205 | 20020205 | (BINARY) | AUTH |
| 2 | 1 | 3 | 4 | 3 | 2 | 20020601 | | | PENDING |

FIG. 6G

Prior Art

*METADATA FILE EXCERPT 320*

```xml
<PATIENT>
    <LASTNAME> GAGE </LASTNAME>
    <MIDDLEINITIAL> P </MIDDLEINITIAL>
    <FIRSTNAME> PHINEAS </FIRSTNAME>
    <PATIENTID> A3665C92 </PATIENTID>
    <PATIENTSBIRTHDATE> 18231025 </PATIENTSBIRTHDATE>
    <PATIENTSSEX> M </PATIENTSSEX>
    <CITY>CAVENDISH </CITY>
    <STATE>VERMONT </STATE>
    <COUNTRY>USA </COUNTRY>
    <STUDY>
        <ACCESSIONNUMBER>74382</ACCESSIONNUMBER>
        <STUDYDATE> 18480913 </STUDYDATE>
        <STUDYTIME> 112405.000 </STUDYTIME>
        <REFERRINGPHYSICIANSNAME> JOHN^MARTYN^HARLOW </REFERRINGPHYSICIANSNAME>
        <STUDYINSTANCEUID> 1.3.46.670589.5.2.7.5524983643.1026922850.514802 </STUDYINSTANCEUID>
        <SERIES>
            <MODALITY>  M  </MODALITY>
            <PATIENTID>  A3665C92 </PATIENTID>
            <BODYPARTEXAMINED> HEAD </BODYPARTEXAMINED>
            <SERIESINSTANCE UID> 1.3.46.670589.5.2.7.5524983643.1026922850.541636 </SERIESINSTANCEUID>
        </SERIES>
    </STUDY>
</PATIENT>
```

*FIG. 10A*

METHODS AND SYSTEMS FOR MANAGING DISTRIBUTED DIGITAL MEDICAL DATA

CROSS REFERENCE TO RELATED APPLICATIONS

This application is a Divisional of U.S. patent application Ser. No. 10/222,056, filed Aug. 16, 2002 and is related to U.S. patent application Ser. No. 10/222,720, titled: METHODS AND SYSTEMS FOR MANAGING PATIENT AUTHORIZATIONS RELATING TO DIGITAL MEDICAL DATA, by inventors: Menschik, Elliot D., Corio, Christopher R., Davis, Wayne F., Didizian, Haig C., filed on same date therewith, now U.S. Pat. No. 7,234,064.

TECHNICAL FIELD

The present invention relates to methods and systems for providing a peer-to-peer network for managing digital healthcare data.

BACKGROUND

The practice of medicine is an information-intensive enterprise. A significant portion of a doctor-patient interaction comprises the collection of historical patient information critical to the successful diagnosis and management of disease. A common and longstanding problem relates to the movement of patients between different health care providers within affiliated medical entities and between unaffiliated medical entities, 20 such movement typically stranding the patient's historical medical information at the source institution.

Historically, this problem stems from the paper-based representation of patient medical information, such paper files requiring the burdensome process of copying and mailing to share with others. Laws and regulations relating to patient privacy and information security compounded the difficulty of paper file sharing. However, even as healthcare providers move to adopt digital representations and management of medical information, significant barriers remain to the sharing and transmission of patient information between providers.

Existing medical information management systems are typically categorized by the types of information they handle. For example: picture archiving and communication systems (PACS) handle the storage and retrieval of digital images, radiology information systems (RIS) handle patient demographics, exam scheduling, and storage and retrieval of radiology reports, laboratory information system (US) are responsible for the storage and retrieval of lab results, hospital information systems (HIS) handle patient demographics, payer information, scheduling and coordination of care across the hospital, computerized patient order entry (CPOE) systems take instructions from physicians as to patient care and distribute tasks to other caregivers, and electronic medical record (EMR) systems handle the digital acquisition and retrieval of the complete patient record often relying upon a storage system termed a clinical data repository (CDR).

A topic of great importance to the medical community is the means by which these existing systems can be integrated within and across given healthcare enterprises. In some instances, Internet web technologies have been applied to provide standard user interfaces by which patient information is shared between affiliated medical institutions through local area networks (LANs) or wide area networks (WANs). One major initiative sponsored by the Radiological Society of North America (RSNA) and the Healthcare Information Management and Systems Society (HIMSS), entitled "Integrating the Healthcare Environment" or IHE, is developing "plug-and-play" interoperable components that manage patient care and workflow within a single health care system. See Siegel, E. L. & Charmin, D. S. 2001 Integrating the Healthcare Enterprise: a primer. Part 1. Introduction. *Radiographics* 21, 1339-41, Channin, D. S. 2001a Integrating the Healthcare Enterprise: a primer. Part 2. Seven brides for seven brothers: the IHE integration profiles. *Radiographics* 21, 1343-50, Channin, D. S., Parisot, C., Wanchoo, V., Leontiev, A. & Siegel, E. L. 2001a Integrating the Healthcare Enterprise: a primer: Part 3. What does IHE do for ME? *Radiographics* 21, 1351-8, Henderson, M., Behlen, F. M., Parisot, C., Siegel, E. L. & Channin, D. S. 2001 Integrating the healthcare enterprise: a primer. Part 4. The role of existing standards in IHE. *Radiographics* 21, 1597-603 and Channin, D. S., Siegel, E. L., Carr, C. & Sensmeier, J. 2001b Integrating the healthcare enterprise: a primer. Part 5. The future of IHE. *Radiographics* 21, 1605-8.

However, to the best of applicants' knowledge, there exist no platforms that support integration and digital information sharing at the cross-institutional level, particularly between unaffiliated medical institutions. This failing stems from several critical outstanding obstacles.

In large part, medical data remains largely analog in nature, that is, paper- and film-based. When patient information is contained in digital form, the formats are typically without accepted or implemented standard representations. Some communications standards, however, do exist. HL7 is a standard for electronic data interchange in healthcare environments. Originally developed in 1987 by a group of large healthcare providers who met at the University of Pennsylvania, the standard at first emphasized point-to-point transmission of patient-oriented admission/discharge/transfer (ADT), order, and results information in inpatient environments. Today, HL7 prescribes formats for the interchange of information concerning all aspects of the healthcare enterprise, including billing, clinical pathways, care guidelines, referrals, and information about practitioners.

One general area of medical practice overcoming the above-described obstacles to standardized digital data sharing is that of radiology, or diagnostic imaging, where a great deal of patient information is either inherently digital (e.g. magnetic resonance imaging, computed tomography, positron emission tomography, etc.) or acquired digitally (computed radiography, digital radiography). Over the last ten years, hospitals have not only adopted digital radiological systems in large quantity, but are also implementing PACS for storing, interpreting and distributing images in their original digital form. The field of radiology is also a leader with respect to digital data standards, having created and adopted the Digital Imaging and Communication in Medicine or DICOM standard, which is universally accepted and implemented around the world. See 2001 *Digital Imaging and Communication in Medicine (DICOM)*. NEMA Publications PS S.1-PS 3.12. Rosslyn, Va.: The National Electrical Manufacturers Association (see http://medical.nema.org).

The successes of modern diagnostic imaging have resulted in limited solutions to cross-institutional communication challenges. These solutions, however, are generally restricted to the sharing of digital data between affiliated entities such as hospitals and clinics within a single health system. One early effort begun in 1991 by Martinez and colleagues at the University of Arizona was the "Global PACS" project (Martinez 1996) which sought to use a non-DICOM standard (the Open Software Foundation's DCE and CORBA services) to create an Internet Protocol (IP)-network based, distributed custom system that could exist in multiple geographical locations and enable the sharing of data to facilitate remote diagnosis and consultation between physicians in different locations. In operation, Global PACS included the ability to telecommunicate with voice in synchronization with the review of radiological images. The system could operate over the network or other IP protocol network(s). See, for example, Part II, Martinez, R. 1996 Distributed System Software Via NSFNET for Global Picture Archiving and Communications Systems (Global PACS); NSF Project NCR-9106155 (1991-1995): University of Arizona.

The Global PACS pilot project, which ended about 1996, was successful in linking rural healthcare providers to radiology specialists in an urban center. However, it constitutes a proprietary system that cannot operate with commercial PACS or other "off-the-shelf" components now in widespread hospital use. Further, it does not support ad hoc searches for existing patient data. Nor does it support any method of identifying patients or obtaining patient authorization as would be necessary to transfer data between unaffiliated medical institutions.

In further recognition of the-potential for the Internet to connect geographically dispersed healthcare providers, Pinksy and colleagues disclosed three methods and apparatuses that, collectively, created a "radiology healthcare network" capable of sharing radiological information across multiple entities. Their disclosure describes a system by which digital diagnostic imaging information could be routed to radiologists around the world for interpretation, with the resulting radiology reports returned to the source institution. See U.S. Pat. Nos. 5,513,101, 5,655,084 and 5,469,353, all to Pinsky et al.

Although the Pinsky et al. system represented an advance for matching the supply and demand of medical images and interpreters, their system is inherently a "push" system that sends data to specified recipients. The system does not permit an arbitrary user (e.g. an authorized physician) to search the network for a user-specified patient and view or transfer images or reports relating to that patient. In addition they provide no means of securing information as it moves between entities. Nor do they provide for patient identification and authorization to support data sharing between unaffiliated institutions.

Another limitation of Pinsky et al. is a system architecture requiring images to move through a central "administrative" site, thereby creating a bottleneck for information as the number of participating institutions accessing large data sets rises. Further, the invention is applicable only to images and waveforms that require interpretation of some sort and would benefit from such a distribution system for sharing workflow.

A similar proposal, burdened with generally the same deficiencies in terms of scalability and cross-institutional applicability as Pinsky et al., was published by Wilson and colleagues, Wilson et al., in 1995, and termed "virtual PACS." Like the invention of Pinsky et al., the proposed system was for sharing radiology-specific workflow. Wilson et al. further included a proposed "single patient folder" for organizing content on multiple servers relating to a single patient. Wilson et al. also introduced the notion of pre-fetching across multiple sites, enabling the retrieval from other servers on the network of a patient's historical studies for use by an interpreting radiologist. See Wilson, D. L., Prior, F. W. & Glicksman, R. A. 1995 Virtual PACS, open systems, and the National Information Infrastructure. *Proc SPIE* 2435, 553-563.

This same group of collaborators later extended the "virtual PACS" concept to a system called a "multiple facility PACS". The multiple facility PACS proposed the inclusion of "pull" features, that is, the ability of users to search for patient imaging data across multiple servers, and to visualize the results or transfer the data to another destination. Their proposal discloses the use of web technology through the use of an Internet web browser as a universal interface, and they discuss the need for centralized coordination between multiple image servers. See Wilson, D. L., Glicksman, R. A., Prior, F. W., Siu, K.-Y. S. & Goldburgh, M. M. 1996 Filmless PACS in a multiple facility environment. *Proc SPIE* 2711, 500-509.

Again, this later Wilson et al. system is limited to sharing medical information, specifically radiological, DICOM-based information, between affiliated institutions sharing a common network, common security procedures, and common patient identification system. As the system was proposed, it would not be applicable to multiple, unaffiliated institutions because it did not support necessary patient authorization of data transfer, or authentication methods between entities with no prior relationship. In addition, the latter-proposed Wilson system has problems with scalability due to reliance upon a single web server creating a data bottleneck and total reliance upon DICOM which cannot support more than a few simultaneous associations. Finally, the latter Wilson et al. system does not address other relevant forms of medical information, notably radiology reports which are not typically accessible through DICOM communications.

One recent proposal in the area of management of distributed digital medical information, and one that partially addresses the problem of cross-institutional communication between unaffiliated entities, is the "PACSter" system proposed in an editorial by Channin. See Channin, D. S., Opinion: Is it Time for 'PACSter'?, Journal of Digital Imaging, Vol. 14, No: 2 (June), 2001: pp 52-53. Channin proposes that PACS-enabled institutions could share imaging data in a purely, or "true," peer-to-peer fashion. The name for this system could be misinterpreted in that the Channin system is a pure peer-to-peer approach, lacking central coordination, and similar to that approach taken by systems such as Gnutella, BearShare, et. al. This is in contrast to the centrally-mediated, peer-to-peer approach of the namesake Napster system. To the best of applicants' knowledge, the Channin system was never actually built.

The PACSter proposal addresses several of the problems with earlier inventions in this area, including its general extensibility to any form of medical information, the direct transfer of medical data between "peers" avoiding bottlenecks at a central location, and a very limited suggestion for using patient attributes to identify, in the absence of a unique identifier, the same patient between two institutions. It is noted that Channin does not propose an actual solution, but merely suggests that it should be possible to use multiple pieces of patient information to match patients.

While this Channin proposal represents a proposal for cross-institutional, peer-to-peer sharing of imaging data between unaffiliated institutions, Applicants believe that its pure peer-to-peer architecture is not workable in a practical implementation for reasons including lack of scalability, lack of reliability, lack of security, an inability to apply the system to generalized situations, and an absence of patient authorization mechanism for data transfer. With respect to scalability, true peer-to-peer networks such as Gnutella require that queries for data be sent to all known participants. These queries are then propagated to participants known to those participants, and so forth. As such there is no guarantee that all entities are connected and it is possible if not likely some requests may never reach a destination entity actually having the sought after data. Further with respect to scalability, the system proposed by Charmin includes large latencies due to multiple propagation steps. It is quite difficult for any one peer to know about and/or organize the contents of all the other peers on the network. Further, DICOM and HL7 are insufficient to support peer-to-peer transfer due to their static configuration of IP addresses, i.e. each hospital would need to be hard-wired to accept communications from every other hospital. DICOM supports only a limited number of simultaneous connections, and HL7 does not support queries of any kind.

With respect to the reliability of the Channin-proposed system, reliability and integrity in a peer-to-peer network are dependent on which hospitals are up and running appropriate software at any given point in time. Hospital information systems and PACS in particular are notorious for unreliability, with uptime in the range of about 97% (as compared, for example, to financial systems that may approach 99.999% uptime). This typical unreliability corresponds to nearly 11 full days (or 263 hours of downtime per year). In a true peer-to-peer network, if a peer is down, a request for data will be unanswered even if the desired data exists on that peer.

With respect to the security of the Channin system, there exists no trusted authority known to the applicants with which to establish trusted communication links between medical institutions. Hospitals are typically unaffiliated outside of their immediate group, and there are strong economic and political barriers to trusting one-another. To the best of applicant's knowledge, no $3^{rd}$ party currently exists that can create dynamic associations on-the-fly between two hospitals or a physician and a hospital that have no prior affiliation. Such associations would be difficult if not impossible with a true peer-to-peer network. Moreover, true peer-to-peer networks suffer from potential security exploits in the form of malicious users masquerading as peers. With respect to generalized situations, the PACSter concept is limited to PACS-enabled institutions and fails to address access to and sharing of information by those entities that do not possess such technology.

Finally, Channin does not contemplate a solution to the problem of patients authorizing the transfer of digital data between unaffiliated institutions, a cornerstone of international data privacy regulations including HIPAA in the United States and the Directives of the European Council.

While there have been various disclosures and proposal for methods to connect parties for the purpose of sharing digital medical information, significant obstacles remain to communication between parties not possessing an a priori relationship. Notably lacking are means of identifying data relating to the same patient at different institutions given the absence of unique patient identifiers of national and international scope, and means for efficiently obtaining an authorization from the patient permitting the transfer of his or her data. Moreover, these earlier proposals all suffer from significant drawbacks in scalability of participants in a network be they users or, more importantly, medical institutions providing the data, in security of communications and data transfers, in compliance with data privacy regulations, and in reliability in uptime and hence finding all relevant data. In addition, these earlier proposals do not provide a means of accessing data from information systems that do not support query/retrieve operations (e.g. systems containing only an HL7 interface) nor do they afford users at institutions lacking digital imaging capabilities a means of participating in the network.

As a result of these obstacles and despite the tremendous potential benefit to patients afforded by secure, portable digital information, present-day communication of historical patient data between healthcare providers generally remains limited to the physical transfer of data on paper or film (by hand or conventional mail), or by facsimile transmission of paper records over telephone networks. In every instance the appropriate paper-based authorization of such transfer(s) is authorized by the patient.

There thus exists a need for new and improved methods and systems for managing digital health care information, which solves the problems of the prior art.

SUMMARY

The present invention provides methods and apparatus for creating a secure, centrally-mediated, peer-to-peer network of healthcare providers requiring no pre-existing affiliations or knowledge of each other. The invention enables authenticated and authorized users (such as physicians) located anywhere in the world to securely search for, identify, and use digital patient data for the purposes of patient care and/or research regardless of where the data physically resides and whether or not the user has a formal relationship with the institution possessing the data. The invention is applicable to any digital form of medical data from one or multiple medical institutions within or between cities, states, provinces, regions or countries. The invention provides for patient privacy, patient data security, arbitrary scalability, high reliability, access to legacy non-queryable systems, and participation by medical entities otherwise lacking digital processing capabilities.

In accordance with an embodiment of the invention, there are provided methods and systems, the method operable on a computer for managing distributed medical data, comprising the steps of: identifying, by an agent computer, a patient medical file containing digital medical data relating to a patient; creating, by the agent computer, a metadata file containing attributes relating to the contents of the patient medical file and the location of the patient medical file; transmitting, by the agent computer, the metadata file to a central computer; matching, by the central computer, the metadata file to a plurality of existing database entries, each of the existing database entries including attributes relating to a remotely located patient medical file including attributes relating to the contents of the remotely located patient medical file and attributes relating to the location of the remotely located patient medical file; and determining, by the central computer, if the metadata file relates to an existing database entry.

In accordance with another embodiment of the invention, there are provided methods and systems, the method operable on a computer for managing distributed medical data, comprising the steps of: receiving, by a computer, a first metadata file containing attributes relating to a remotely stored patient medical file, the first metadata file including attributes relating to the contents of the patient medical file and a location of the patient medical file; extracting the attributes from the first metadata file; processing selected attributes extracted from the first metadata file to place the selected attributes in a standardized format; storing the selected attributes, in the standardized format, in a database entry; receiving a second metadata file containing attributes relating to a remotely stored patient medical file; extracting the attributes from the second metadata file; comparing, by the computer, the attributes from the second metadata file to the attributes stored in the database entry; and determining, by the computer, if the second metadata file relates to the database entry.

In accordance with another embodiment of the invention, there are provided methods and systems, the method operable on a computer for managing distributed medical data, comprising the steps of: identifying, periodically on a programmed basis, a plurality of patient medical files each containing digital medical data relating to a patient; creating, for each of the plurality of patient medical files, a metadata file containing attributes relating to the contents of the patient medical file and the location of the patient medical file; packaging each of the metadata files for transmission to a remote central computer; and transmitting, in a secure manner, each of the metadata files to the remote central computer.

In accordance with another embodiment of the invention, there are provided methods and systems, the method operable on a computer for managing distributed medical files, comprising the steps of: receiving, on a central computer, a request to access a patient medical file stored on a remote medical information system; determining a remote agent computer having access to the remote medical information system; transmitting, from the central computer to the remote agent computer, a request to provide-the patient medical file to a specified device; retrieving, by the remote agent computer, the patient medical file; transmitting, by the remote agent computer, the patient medical file to the specified device; and transmitting, by the remote agent computer to the central computer, a notice that the patient medical file has been transferred from the remote medical information system to the specified device.

In accordance with yet another embodiment of the invention, there are provided methods and systems, the method operable on a computer for managing distributed medical files, comprising the steps of: receiving, on a central computer, a request to obtain a remotely stored patient medical file; determining, by the central computer, a remote first agent computer having access to the medical information system storing the patient medical file; transmitting, by the central computer to the remote first agent computer, a request to obtain the patient medical file and to transmit the patient medical file directly to a specified device; and receiving, on the central computer from the remote first agent computer, a notice that the patient medical file has been transferred from the medical information system to the specified device.

In accordance with another embodiment of the invention, there are provided methods and systems, the method operable on a computer for sharing distributed medical records, comprising the steps of receiving from a central computer a request to obtain an identified patient medical file from a medical information system and to transmit the identified patient medical record directly to a specified device; retrieving the identified patient medical file from the medical information system; transmitting the identified patient medical file directly to the specified device; and transmitting to the central computer a notice that the identified patient medical file has been transmitted to the specified device.

And in accordance with yet another embodiment of the invention, there are provided methods and systems, the method operable on a computer for managing distributed medical files, comprising the steps of: storing, by a computer, a database entry containing standardized attributes relating to a remotely stored patient medical file at a storage location, the standardized attributes relating to the contents of the patient medical file and the storage location of the patient medical file; receiving a search request including patient medical data attributes; comparing the patient medical data attributes in the search request to the standardized attributes in the database entry to determine if, in the absence of a unique identifier attribute; the search request identifies the remotely stored patient medical file; and initiating, if the search request identifies the remotely stored patient medical file; a request to release the remotely stored patient medical file to a user.

BRIEF DESCRIPTION OF THE DRAWINGS

These and other objects, features and advantages of the invention will become apparent through a consideration of the Detailed Description of the Invention in conjunction with the Drawing Figures, in which:

FIGS. 6A-G are tables showing exemplary database entries in the central system;

FIG. 10A is a table showing an exemplary excerpt from a metadata file of the type generated by an agent for use by the central system;

DETAILED DESCRIPTION OF ILLUSTRATIVE EMBODIMENTS

Figure 1:
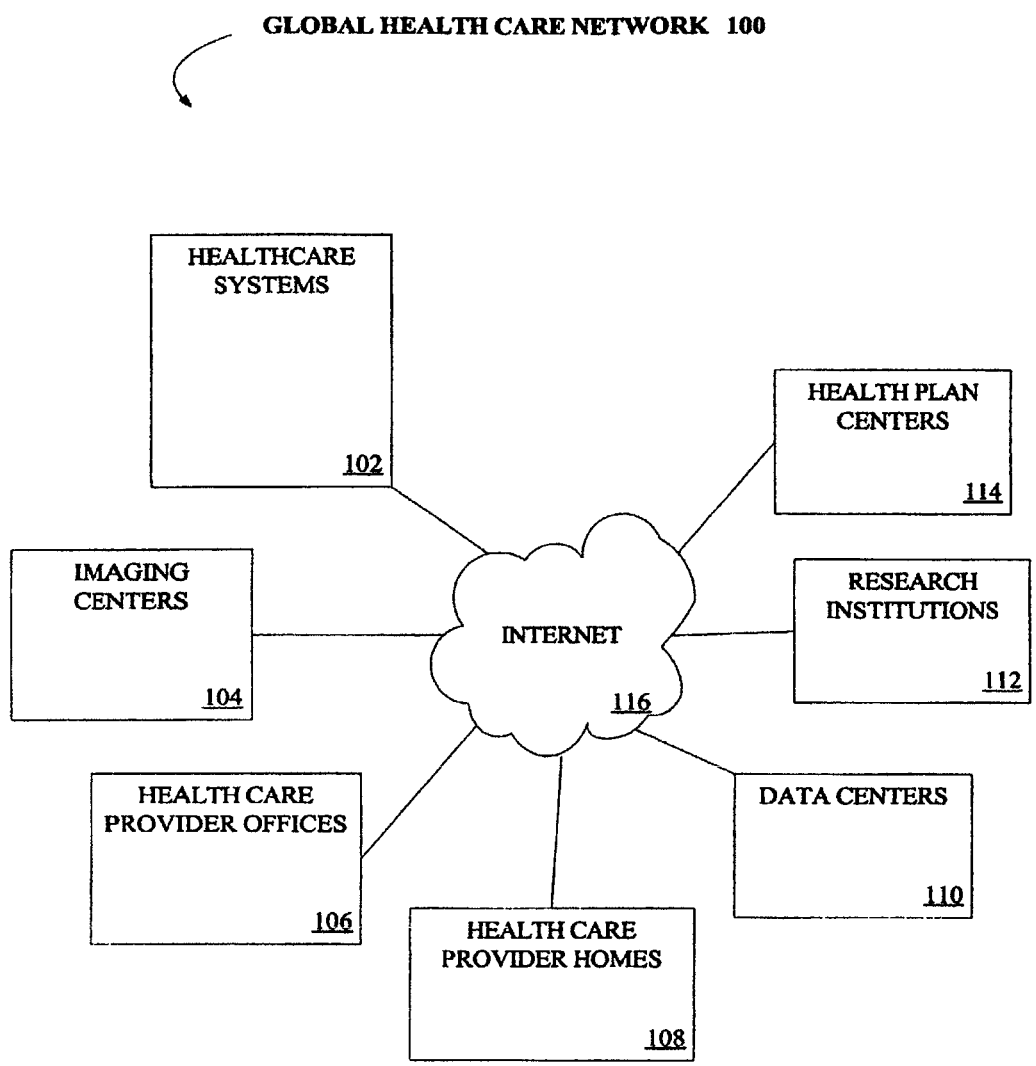
FIG. 1 is a block diagram of an exemplary global health care network.

The present invention, described in detail below, comprises a distributed network including one or more central systems each supporting distributed agents for managing the peer-to-peer sharing of digital patient medical data, in the form of medical data files or streaming data, amongst participating health-care-providers such as hospitals and physicians.

Generally, each participant in the distributed network supports a local network agent responsible for identifying digital patient medical data stored by the participant. Existing and newly generated patient medical data is identified by the local agent, which in turn generates a metadata file (i.e. data about data) of identifying information for each file of patient medical data, the metadata file being transmitted to the central system for parsing and storage in the database which serves as an index of available data for all network participants.

Upon receipt, the central system parses each metadata file and compares it to existing entries in database tables to determine if the incoming metadata file identifies medical data for a new or existing patient. If the incoming metadata file identifies new medical data for an existing patient or medical data for a new patient, that metadata file is used to create a new set of entries in the database tables of the central system.

Authenticated users, such as doctors, can query the central system; searching the database entries for entries identifying patient medical records that may be stored at any of the distributed network participants. If a database entry identifying patient medical data is located on the central system, a process is provided for digitally obtaining a patient's authorization to release that medical data from the source healthcare participant currently storing, or 'owning,' the medical data to the user.

After authorization by the patient, the authenticated user can request access to the remote patient medical data still in storage at the source participant, either by requesting a transfer of the patient medical data or by requesting to view the patient medical data. The central system then mediates a peer-to-peer transfer or viewing between the agent at the participating source and the agent or user interface (e.g. a web browser) at the user site.

As will be shown below, the invention has particular application in wide area network health care systems including many participants over a wide geographic area. The invention provides for patient-centric organization of patient medical data strewn across an arbitrary number of medical institutions, and facilitates the finding and viewing of potentially critical patient medical records, which, due to remote locations and/or confinement within a participating institution, may otherwise be undiscoverable. The patient authorization process facilitates the simple but effective and secure obtaining of a patient authorization to release the data from the source participant to the user. The network-facilitated, peer-to-peer data transfer and viewing processes facilitate the secure, reliable, timely and inexpensive sharing of the data between the source and user while preserving the-privacy of patients (i.e. medical data is neither stored at nor traverses a central location) and scaling to essentially unlimited numbers of participants. The invention further accommodates the patient release and authorization forms and processes of the data owner or source, which can vary amongst participants, particularly between different institutions whether domestically or internationally.

As will be shown and described below, numerous security practices and procedures are in place to protect the privacy of the patient data by limiting access only to authenticated and authorized users.

With reference now to FIG. 1 there is shown, for purposes of illustration and explanation, an exemplary global healthcare network 100 including one or more each of healthcare systems 102 which may, for example, include one or more hospitals and other health care providers therein, independent diagnostic imaging centers 104, health care provider offices 106, for example physicians' offices, health care provider's homes 108, for example physicians' homes, external data centers 110 that store patient data including radiological imaging data, for example at an "application service provider" (ASP) hosting the data for one or more health systems, research institutions 112, for example universities, contract research organizations (CROs), or other commercial healthcare entities, and health plan centers, 114, for example an HMO center, a third-party payer, or a governmental organization such as the Center for Medicare and Medicaid Services, all connected through a wide area network 116, for example the Internet.

It will be appreciated that the various parties in global health care network 100 include both affiliated and unaffiliated parties, that is, affiliated parties with contractual working relationships that share resources, and totally separate, unaffiliated parties. It will further be appreciated that the various parties are inter- and intra-connected through a wide variety of both internal and external networks, Internet 116 likely comprising the widest area network through which all of the parties ultimately communicate.

Figure 2:
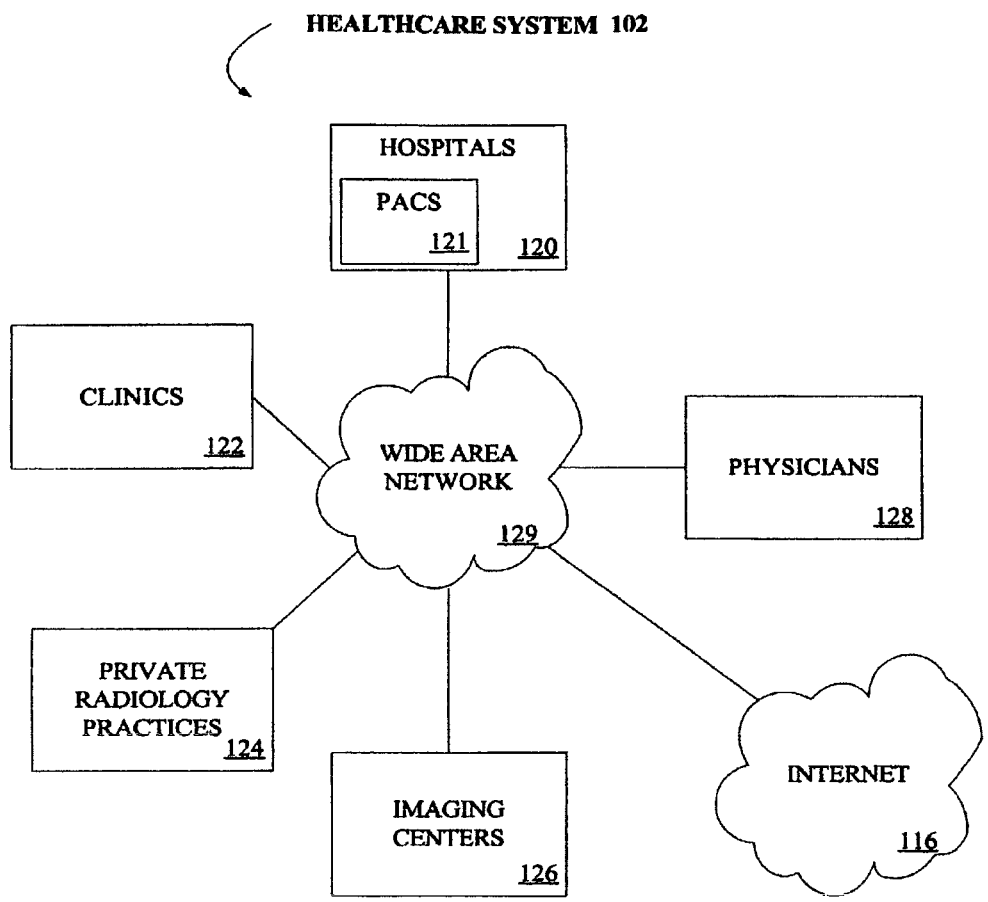
FIG. 2 is a block diagram of an exemplary health care system of FIG. 1.

With reference now to FIG. 2, one exemplary embodiment of healthcare system 102 (FIG. 1) comprises affiliated entities including one or more hospitals 120, clinics 122, private radiological practices 124, imaging centers 126 and physicians 128 who may be working from home, an office, a hospital or another health care environment. At least one hospital 120 is seen to include a picture archiving and communication system (PACS) 121, described in further detail below. The affiliated parties comprising health care system 102 communicate through one or more proprietary local and/or wide area networks 129, the proprietary network connected to Internet 116.

Figure 3:
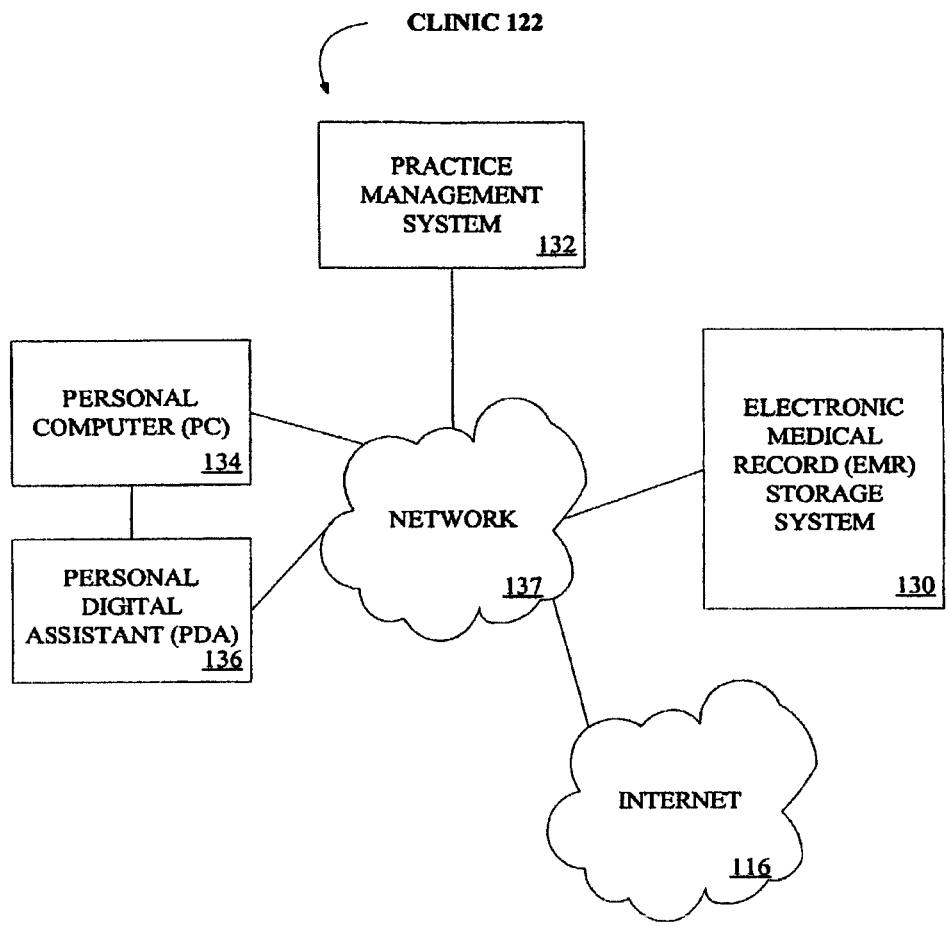
FIG. 3 is a-block diagram-of an exemplary clinic of FIG. 2.

With reference to FIG. 3, one exemplary clinic 122 is shown wherein healthcare providers interact personally with patients. Clinic 122 is seen to include an electronic medical records (EMR) storage system 130, a practice management system 132, and a personal computer and/or a personal digital assistant 136, the latter devices providing human interfaces to the records and practice management system. The various components of clinic 122 communicate through one or more proprietary local and/or wide area networks 137, the proprietary network connected to Internet 116.

Figure 4:
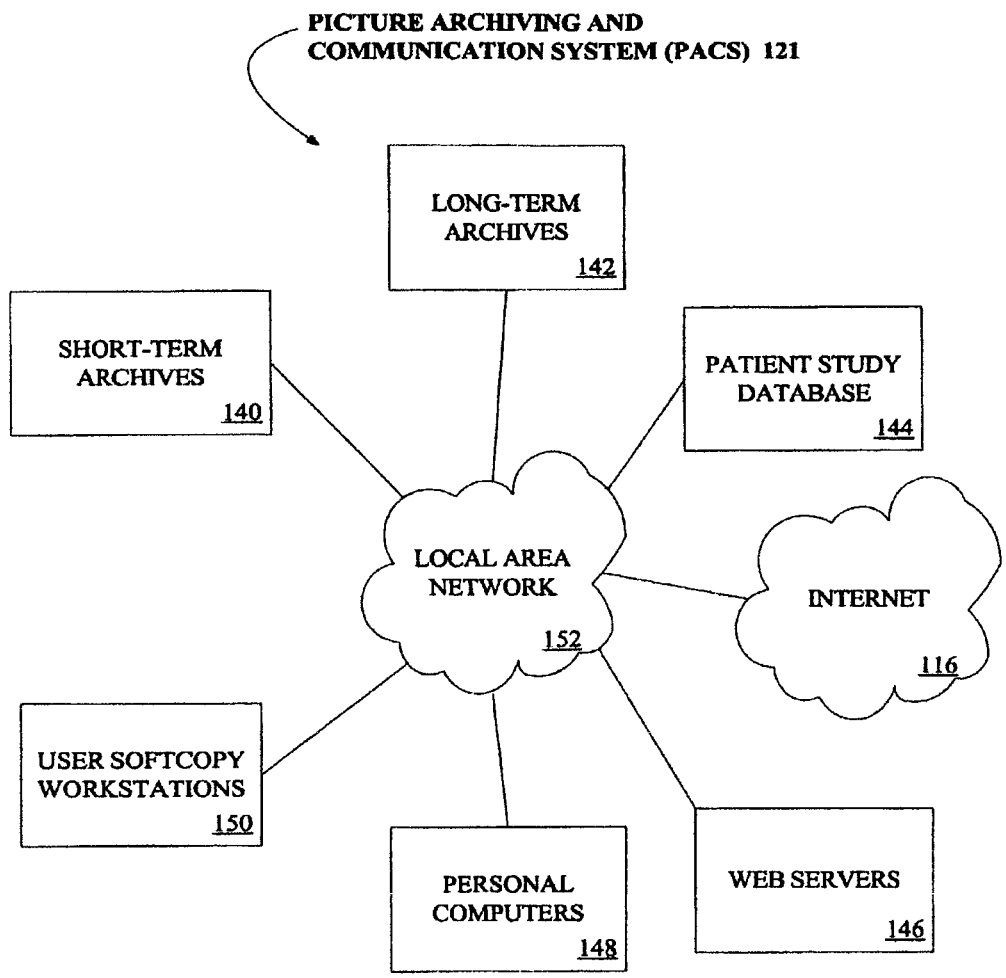
FIG. 4 is a block diagram of an exemplary picture archiving and communications system (PACS)

With reference now to FIG. 4, one exemplary PACS 121 is shown to include short and long-term digital file archives 140, 142, respectively, a patient study database 144 containing individual digital patient medical records linked to stored digital radiological image files contained in the archives, a web server 146 for coordinating access between users and the various archives 140, 142 and database 144, one or more personal computers 148 for providing human user interfaces and one or more user "softcopy" workstations 150 where users such as radiologists can view diagnostic quality (i.e. very high-resolution) images and report on digital patient files. All of the various components of PACS 121 are connected through a local area network 152 of a conventional type, the local area network being connected to Internet 116.

It will be appreciated that the above-described global healthcare network 100 with the exemplary participants and components, as described in FIGS. 1-4, is not exhaustive in its description and that there are literally endless types and configurations of healthcare provider relationships and affiliations that may be contained within such a network. Further, the various networks as described may range-in scope from being limited to a particular geographical region to being internationally distributed.

Important to understand for purposes of the present invention is the need for the various health care providers within global network 100 to share patient medical data. For purposes of the present invention, the patient data of interest is digital data, including both inherently digital data arising, for example, from a magnetic resonance imaging (MRI) scan and digitized data arising, for example, from the conversion of a paper record or analog radiological image into digital format.

It will be understood that the digital patient data of interest include medical records and files stored as digital files, for example of the type resulting from radiological studies. As noted above, many different formats exist for such files, which may be stored in many different types of storage environments or exist as streaming data. Every given healthcare provider typically has multiple storage environments for different forms of medical information and the integration of and linkage between such systems, even within a single entity, is today quite limited or even non-existent. The term "medical information system" is used generically herein to describe all the different types of systems that may store patient medical data files. Disparate and often proprietary data formats, data types and storage hardware make finding stored patient data challenging within a single institution, and even more challenging between multiple affiliated healthcare providers. For unaffiliated entities, the technical challenges, privacy and security issues make patient digital medical record finding and sharing effectively impossible.

Figure 5:
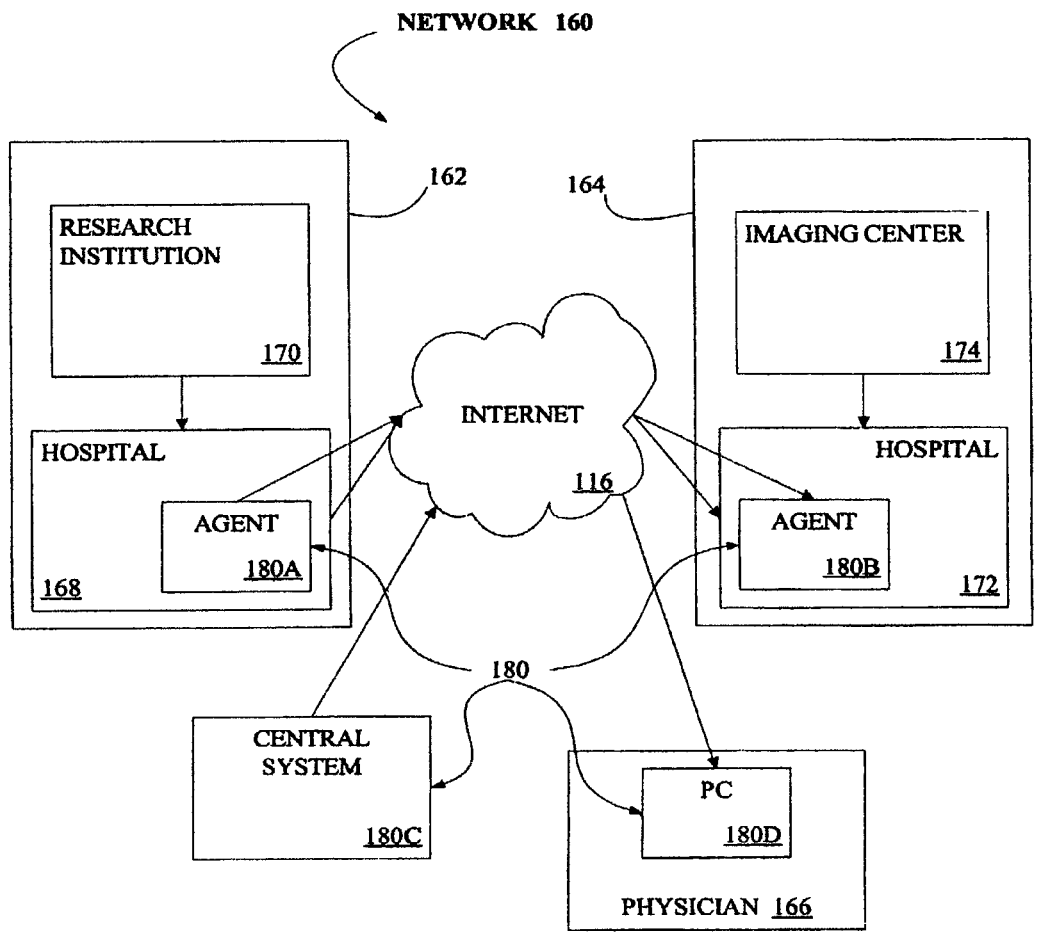
FIG. 5 is a block diagram of a portion of a global health care network incorporating a centrally mediated, peer-to-peer file transfer system in accordance with the present invention.

With reference now to FIG. 5 there is shown a distributed healthcare network 160 comprising an exemplary portion of global healthcare network 100 (FIG. 1) incorporating features of the present invention. Distributed healthcare network 160 includes first and second, unaffiliated health care systems 162, 164, respectively, and a physician 166 who may or may not be affiliated with one of the health care systems. Health care system 162 includes a hospital 168 having affiliated therewith a research institution 170. Health care system 164 includes a second hospital 172 having affiliated therewith a stand-alone imaging center 174.

In accordance with the present invention, each of healthcare systems 162, 164 and physician 166 in network 160 is associated with a centrally mediated, distributed network 180. Distributed network 180 includes a remote agent 180A disposed in hospital 168, a remote agent 180B disposed in hospital 172, a central system 180C and a personal computer 180D, one possible human interface through which the physician 166 can interact with the network. All of the various participants in network 160 communicate through a wide area network such as Internet 116 through conventionally known connections.

It will be appreciated that privacy and security are important to the communication of health-related data. In the described embodiment, the various components of distributed network 180 communicate securely over Internet 116 using IP Security (IPSec) protocols, a point-to-point security system well known, used to provide secure communications over the Internet for particularly sensitive transactions between a finite and known number of parties, and which to date has been proven extremely secure. Alternatively, other security schemes can be used, and/or network 180 may be configured to communicate over a private, dedicated network.

As is described in detail herein below, agents 180A & B function to collect certain metadata from their respective source hospitals (e.g. patient demographic data, the date, time and form of medical data, etc. but not the content of the medical data). This collected 20 metadata is stored in a metadata file and transmitted to central system 180C for parsing and indexing for use in facilitating user searches to identify digital patient medical records. Selected digital patient medical records, once searched and identified by an authenticated user such as a physician and authorized for release by a patient, are shared by dedicated peer-to-peer digital medical data file transfers between the various data sources, users and other authorized participants in network 160.

Figure 6:
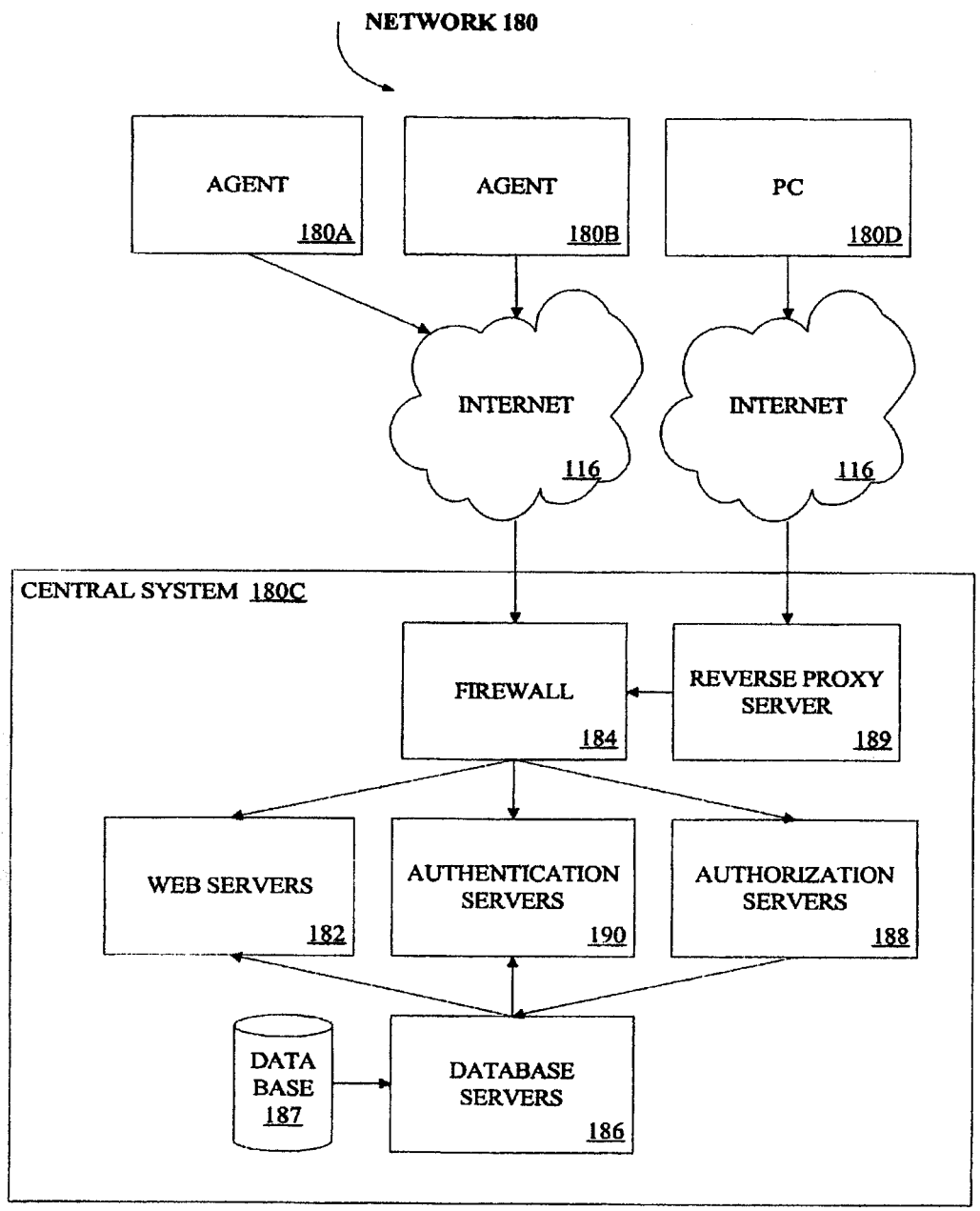
FIG. 6 is a block diagram of the central system of FIG. 5.

With reference now to FIG. 6, a more detailed view of distributed network 180 is shown, with central system 180C seen to include web servers 182, authorization servers 188 and authentication servers 190 connected to database servers 186 supporting a database 187, all behind a firewall 184. The web, authorization, and authentication servers are accessed by "reverse" proxy servers 189 that exist outside the firewall and which communicate through the firewall via a highly limited protocol with the respective servers. Agents 180A, B connect directly to the server components of central system 180C behind the firewall 184, while a physician PC 180D is shown connected to central system 180C through a reverse proxy server 189 connected to Internet 116 and outside the firewall 184. The reverse proxy server is in turn connected to firewall 184.

In operation, reverse proxy server 189 and firewall 184 function in a known manner to provide secure access to the remaining servers within central system 180C. Web servers 182 function in a known manner to manage incoming and outgoing communications via Internet 116. Database servers 186 function to manage the storage and retrieval of data from database 187, the data of the type described herein. Authentication servers 190 function to authenticate users requesting access to data in a manner described below, while authorization servers 188 function to secure and process patient authorizations, also in a manner described below.

The various servers 182, 186, 188 and 190 within central server 180C can comprise any conventional computer server capable of performing the functions described herein. One exemplary embodiment for such servers includes a VA Linux FullOn 2×2 model 2230 2U rack-mountable server with a single Pentium™ III 500 MHz processor, 1 GB of RAM and one 9 GB UltraSCSI hard drive, running the ultra-secure OpenBSD 3.1 operating system and the Squid 2.5 proxying/caching server software, the OpenSSL secure socket layer software, and the PHP 4.1 hypertext processor to act as the reverse-proxy server and a Dell PowerEdge 4400 7U rack-mountable with dual Pentium™ III Xeon™ 933 Mhz processors, 2 GB of RAM, eight 18 GB UltraSCSI drives with a hardware-based RAID10 configuration, running the RedHat distribution of the Linux operating system (version 7.3), the Oracle 8i database server for Linux, the Apache 1.3 web server, and the PHP 4.1 hypertext processor. Again, many different configurations will be known.

With reference now to FIGS. 6A-6G, there are shown exemplary database tables for storing relevant data, extracted from metadata files then standardized in a manner described below, in database 187 of central system 180C. As is described below, the Page 21 of 73 entries in the tables of database 187 are created as metadata files by the distributed agents and transmitted to the central system, where they are parsed and their contents imported. It is understood that these exemplary tables focus upon the storage of metadata pertaining to diagnostic imaging data for illustrative purposes and the present invention is likewise applicable to other forms of digital medical data that have been omitted for the sake of clarity and brevity.

FIG. 6A shows a database table 191 storing names associated with a given person identifier (with such person identifiers being unique within database 187 of the invention's central system 180C) including 8 entries 191-1 through 191-8, each entry including 9 fields containing person identification information, comprising: a person identifier (PEOPLE_ID 191A) uniquely identifying each person in the system, including patients, physicians, administrators, etc., a person title (TITLE 191B), a person first name (FIRST 191C), a person middle name (MIDDLE 191D), a person last name prefix (LAST_PRE 191E), a person last name (LAST 191F), a person name generational suffix (GEN 191G), and first and second person occupational suffix fields (OCC1 191H AND OCC2 191I).

FIG. 6B shows a database table 192 storing addresses including 4 entries 192-1 through 192-4, each entry including 10 fields containing address information for people and/or institutions, comprising: a unique address identifier (ADDR_ID 192A), an address number (NUM 192B), an address street name (NAME 192C), an address street type (TYPE 192D), a within-structure type (e.g. Apartment) (WITHIN 192E), a within-structure identifier (WITHIN_ID 192F), an address city identifier (CITY 192G), an address state identifier (ST 192H), a postal code (POSTAL 192-I) and an address country (COUNTRY 192J).

FIG. 6C shows a database table 193 storing unique institution names, including 2 entries 193-1 through 193-2, each entry including 2 fields containing medical service facility information, comprising: a unique medical institution identifier (INST_ID 193A) and a medical institution name (INSTITUTION NAME 193B).

FIG. 6D shows a database table 194 mapping a given patient to an arbitrary number of medical record numbers identifying that patient at an arbitrary number of medical institutions, including 3 entries 194-1 through 194-3, each entry including 3 fields containing medical record number information, comprising: a medical record number (MEDICAL_RECORD NUMBER 194A), the unique person identifier (PEOPLE_ID 194B) identical to that assigned a patient as PEOPLE_ID 191A in FIG. 6A above, and a medical institution identifier (INST 194C) identical to that assigned an institution as INST_ID 193B in FIG. 6C above. It will be understood that the medical record numbers and institution identifiers associated with each unique person identifier are used to identify the patient (FIG. 6A) in association with one or more specific medical facilities (FIG. 6C).

FIG. 6E shows a database table 195 storing information specific to a single diagnostic imaging study including 2 entries 195-1 through 195-2, each entry including 7 fields containing medical study information, comprising: a unique study identifier (STUDY_ID 195A), an institution identifier (INST_ID 195B) and a patient identifier (PATIENT_ID 195C), each identical to the identifier assigned in the corresponding PEOPLE_ID and INST_ID fields in FIGS. 6A and 6C, a study date (DATE 195D), a study accession number generated by the scheduling system that ordered the study (ACCESSION NUM 195E), an ISO and DICOM-compliant unique study instance identifier (STUDY INSTANCE UID_195F), and a referring physician identifier (REFERRING_PHYSICIAN_ID 195G).

FIG. 6F shows a database table 196 storing information specific to a series of diagnostic images associated with a particular diagnostic imaging study including 6 entries 196-1 through 196-8, each entry including 6 fields containing radiological image series information, comprising: a unique series identifier (SERIES-ID 196A), a study identifier (STUDY_ID 196B) identical to the STUDY_ID field of FIG. 6E, a study modality (MODALITY 196C), an ISO- and DICOM-compliant series instance unique identifier (SERIES_INSTANCE_UID 196D), a series body part identifier (BODY_PART 196E) and a series laterality indicator (LATERALITY 196F).

With reference now to FIG. 6G, a database table 197 including 2 entries 197-1 through 197-2, each entry including 9 fields, contains patient authorization information, comprising: a unique authorization identifier (AUTH_ID 197AA), an authorization form identifier (FORM_ID 197B), a physician identifier (PHYSICIAN_ID 197C), a patient identifier (PATIENT_ID 197D), an institution identifier (INST_ID 197E), a request date (REQ_DATE 197F) indicating the date the authorization request was submitted, an authorization date (AUTH_DATE 197G) indicating the date the patient authorization was granted, a binary representation of the actual patient authorization signature (SIGNATURE 197H) and a status (STATUS 197I) indicating the status of the authorization as pending (i.e. not authorized) or authorized.

Again, it will be understood that unique entries spanning multiple database tables, including the PHYSICIAN_ID, PATIENT_ID AND INST_ID contain consistent identifying data from table to table. For example, the PATIENT_ID fields in tables 194, 195, and 196 all include like data, a single patient identifier, for example patient identifier "1", identifying the same patient in each table and identical and corresponding to a person in the PERSON_ID field of table 191. It will thus be understood that, as is further described below, the database tables 191-197 in database 187 contain indexed, identifying information of patients and identifying information of digital medical data records relating to those patients. It will further be understood that the actual patient records including the large digital medical data files associated with the records, continue to reside with the source participant healthcare provider, i.e. the hospital, imaging center or other medical data record source originally generating and/or currently storing such data.

As described in further detail below, a search of the database tables in FIG. 6A-G is used to find and identify remotely stored digital patient medical records.

Figure 7:
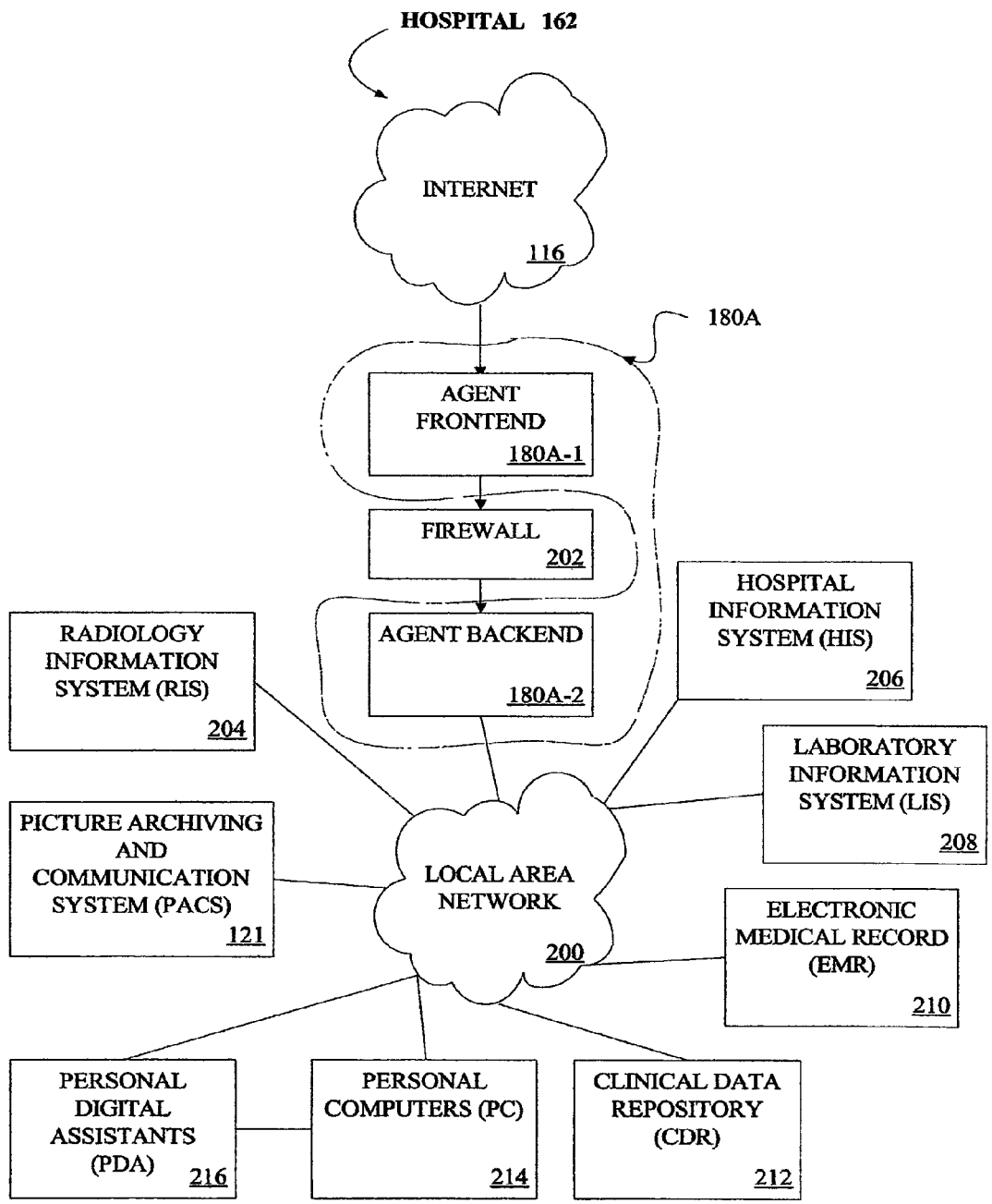
FIG. 7 is a block diagram of the hospital of FIG. 5 incorporating a distributed agent in accordance with the present invention.

Discussing now FIG. 7, one exemplary detailed embodiment of hospital 162 is shown, incorporating distributed agent 180A in accordance with the invention. It will be understood that this description is exemplary of the installation and operation of distributed agent 180A, a similar one of which is installed and operated at all participants in distributed network 180.

Hospital 162 is seen to include a variety of interactive functions interconnected through a conventional local area network 200 and contained within a firewall 202. The various functions incorporated within hospital 162 include one or more each of: a PACS 121 of the type described with respect to FIG. 4 above, a radiology information system 204, a hospital information system 206, a laboratory information system 208, an EMIR system 210, a clinical data repository 212, and personal computers 214 and personal digital assistants 216.

Agent 180A is seen to include a front-end 180A-1 serving as an interface between Internet 116 and firewall 202, the front-end functioning as a reverse proxy server. An agent backend 180A-2 is connected between firewall 202 and local area network 200, agent 180A thus accommodating secure communications between local area network 200 and Internet 116 such that compromise of the front-end 180A-1 by a malicious user intent on penetrating the firewall 202 will not permit access to the local area network.

As described above, PACS 121 is operative to store and communicate digital patient data records of a diagnostic imaging nature. Radiology information system 204 and laboratory information system 208 are typical hospital systems for managing the scheduling functions of the respective departments, i.e. the radiology and laboratory departments as well as the storage of results such as radiology reports, laboratory test values, and pathology interpretations. Hospital information system 206 is for managing the admission, discharge and transfer of patients within the general hospital operation as well as financial functions including claims processing and submission to third-party payers. The electronic medical record system 210, similar functionality to which may or may not also exist in PACS 121, typically permits health-care providers to enter clinical observations and retrieve patient notes and charts (at times including digital images from the PACS 121), while a clinical data repository 212 provides back-end storage for a host of patient records including observations, notes, waveform data (ECG, EEG, etc.) and perhaps duplicate representations of data stored in other specialized information systems. Personal computers 214 and personal digital assistants 216 (PDAs) are for providing standard user interfaces to the various hospital systems, records and repositories. As is described below, PDAs 216 can also be used by patients to provide authorization for the release of medical records.

As will be described in further detail below, agent 180A generates reports in the form of metadata files on patient data for transmission to central server 180C.

Figure 8:
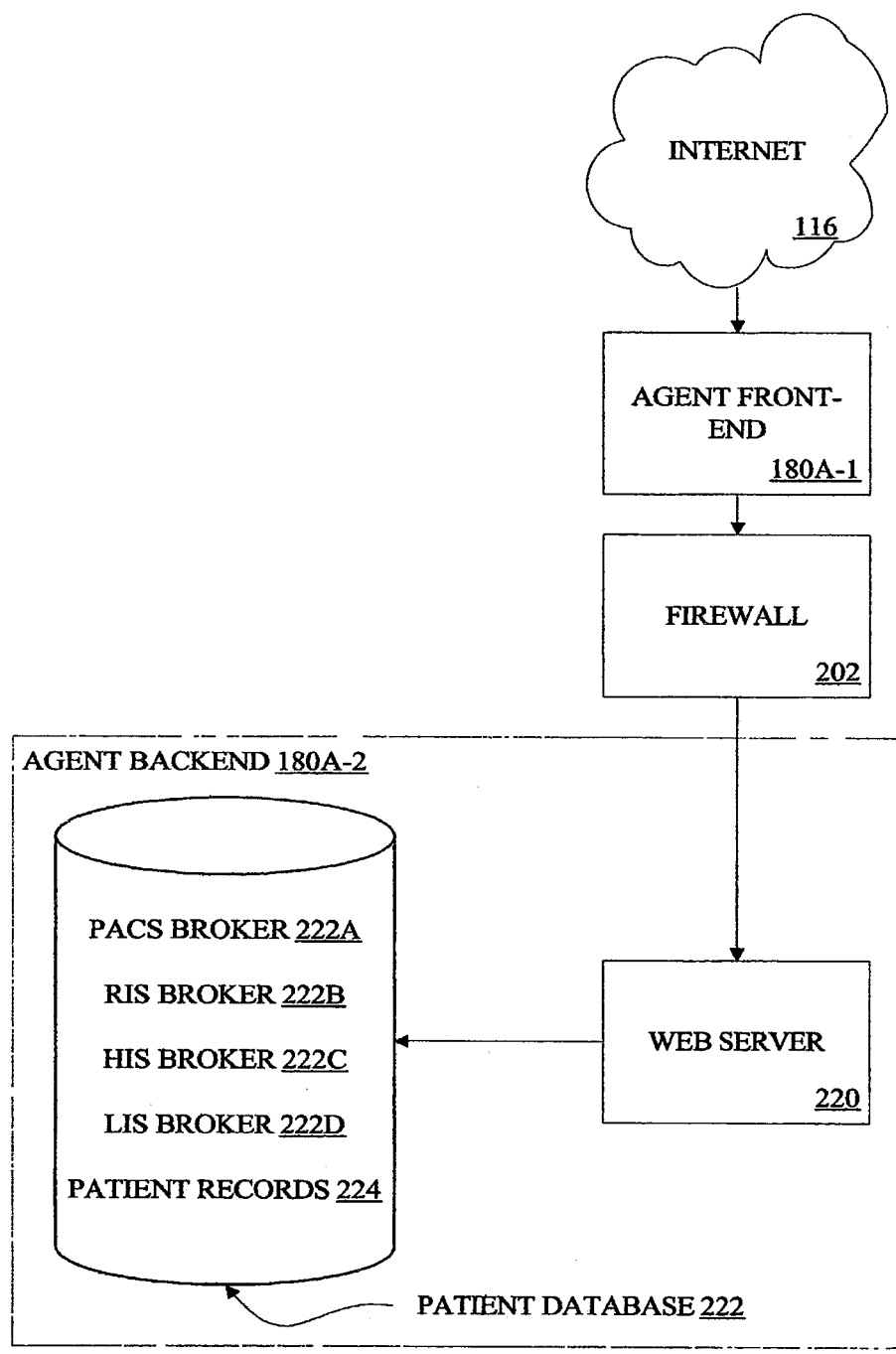
FIG. 8 is a block diagram of the distributed agent of FIGS. 5, 6 and 7.

With reference now to FIG. 8, a more detailed view of agent 180A is shown, the agent including a reverse proxy server front-end 180A-1 connected to a web server 220 of agent backend 180A-2 through firewall 202. Web server 220 is in turn connected to patient database 222 as well as a series of software programs indicated as 'brokers' for communicating with various hospital facilities. Illustrated brokers include a PACS broker 222A for communicating with the PACS system 121, an RIS broker 222B for communicating with radiology information system 204, an HIS broker 222C for communicating with hospital information system 206 and an LIS broker 222D for communicating with laboratory information system 208. It will be understood that the data contained on the various medical information systems, i.e. the PACS, RIS, HIS, LIS, are typically contained in formats proprietary to the particular device. The broker software are processes for obtaining data from the various medical information systems. Many types of medical information systems, each requiring a specific software broker to obtain data there from, are known in the art. It will be appreciated that an essentially unlimited number of brokers can be provided on the agent server described above. Further, these brokers can operate in a 'pull' mode retrieving information from the medical information systems, or in a 'push' mode receiving information transmitted to them.

Figure 8A:
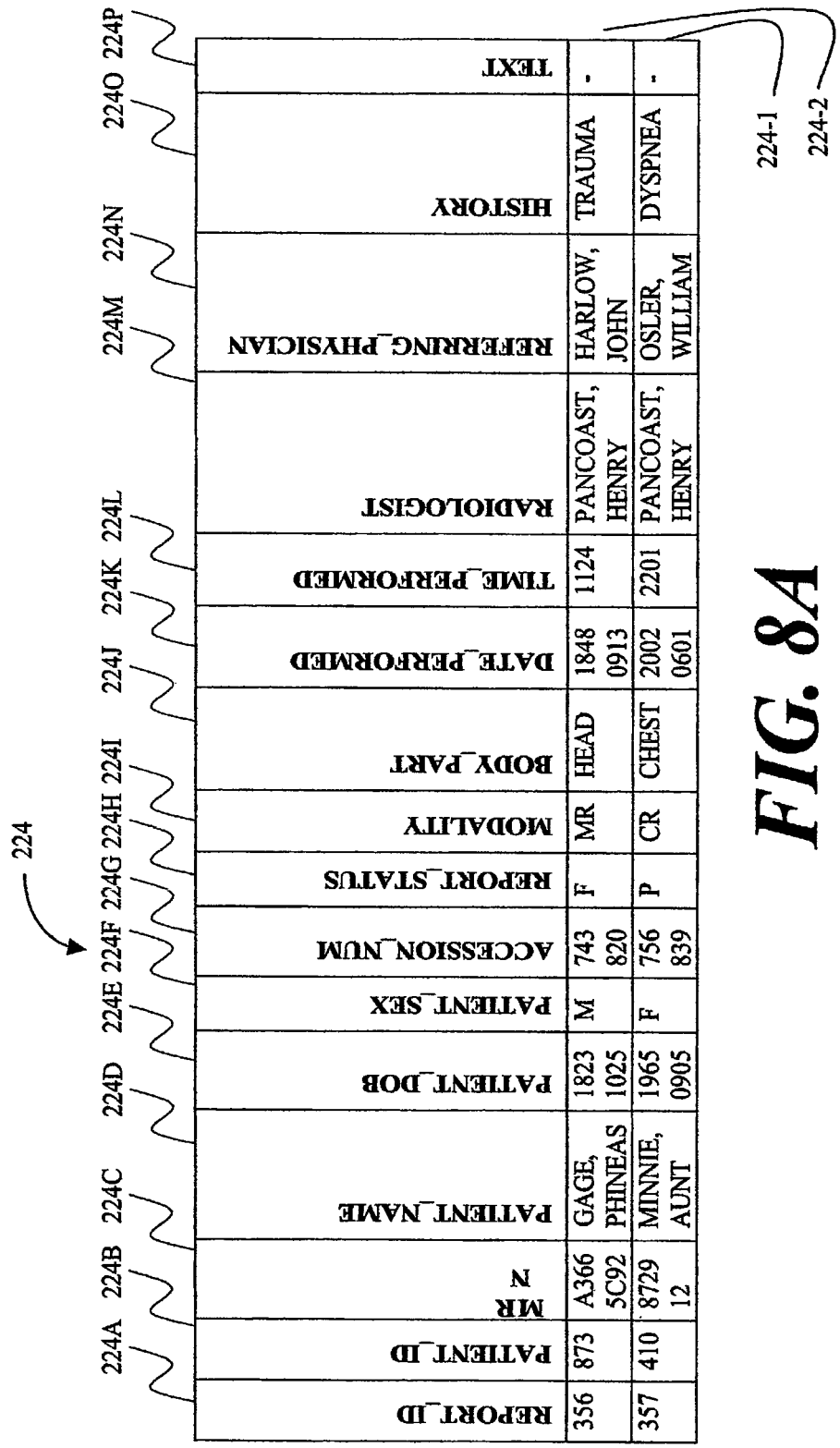
FIG. 8A is a table showing an exemplary database in a distributed agent.

Patient database 222 further stores actual standardized patient records 224 (as opposed to meta-data) which duplicates data residing on hospital systems that cannot be actively queried in an ad hoc fashion, described in further detail with respect to the database table 224 in FIG. 8A. Such patient records 224 are not transmitted to central system 180C but database 222 permits the authenticated and authorized user to query and retrieve such data in a peer-to-peer to fashion where such queries could not be passed on to the appropriate information system due to an absence of support for query and retrieve (the "pull") operations.

Agents 180A & B can comprise any conventional computer server capable of performing the functions described herein. One exemplary embodiment of an agent includes a VA Linux FullOn 2×2 model 2230 2U rack-mountable server with a single Pentium™ III 500 MHz processors, 1 GB of RAM and one 9 GB UltraSCSI hard drive, running the ultra-secure OpenBSD 3.1 operating system and the Squid 2.5 proxying/caching server software, the OpenSSL secure socket layer software, and the PHP 4.1 hypertext processor to act as the front-end (reverse-proxy) component of the agent. Also included is a VA Linux FullOn 2×2 model 2250 2U rack-mountable server with dual Pentium™ III 600 MHz processors, 1 GB of RAM, and two 9 GB UltraSCSI hard drives, running the Debian distribution of the Linux operating system, the Apache 1.3 web server, the PHP 4.1 hypertext processor, the PostgreSQL database server, and FreeS/WAN IPSec implementation as the back-end of the agent. However, many different configurations will be apparent.

Table 224 of FIG. 8A, an example of how one form of patient records (in particular, diagnostic imaging results) may be stored, is seen to include 2 records, 124-1 and 124-2, each record relating to a particular patient diagnostic imaging study performed at hospital 162 and including sixteen data fields, comprising: a unique patient report identifier (REPORT_ID 224A), a patient identifier (PATIENT_ID 224B), a medical record number (MRN 224C) unique to hospital 162, a patient name (PATIENT NAME 224D), a patient date of birth (PATIENT_DOB 224E), a patient gender (PATIENT_SEX 224F), an accession number (ACCESSION NUM 224G) comprising a unique identifier from the RIS that is generated when the study is ordered and used by some medical information systems to call up the status and results of a particular study, a report status indicator (REPORT_STATUS 224H) indicating the completion status of a radiological report (i.e. f=finished, p=preliminary), a modality indicator (MODALITY 224I) indicating the modality which acquired the images (e.g. CT, MR, etc.), a body part indicator (BODY_PART 224J), a date indicating when the study was acquired (DATE_PERFORMED 224K), a time indicating the time on the date the study was acquired (TIME_PERFORMED 224L), the name of the primary radiologist who interpreted the study (RADIOLOGIST 224M), a name of a referring physician if any (REFERRING_PHYSICIAN 224N), a medical history (HISTORY 224O) providing a brief indication for the study, and a text field (TEXT 124P) containing the text of the radiology report.

As will be described in further detail below, patient records 224 within agent back-end 180A-2 are updated periodically, for example each evening, with new patient records from hospital 162. The new patient records are collected, using the appropriate software broker, from one of the various information and/or record systems contained within the hospital whether it is "pulled" by the broker software or whether the broker software is accepting "pushes" from other systems. It will be understood that 'pushed' data is transmitted to the agent broker software at the initiation of the medical information system, while 'pulled' data is retrieved by the agent broker software. In the described embodiment, the diagnostic imaging results stored in patient records 224 are gathered by the RIS broker 222B via communication with the radiology information system 204.

Figure 9:
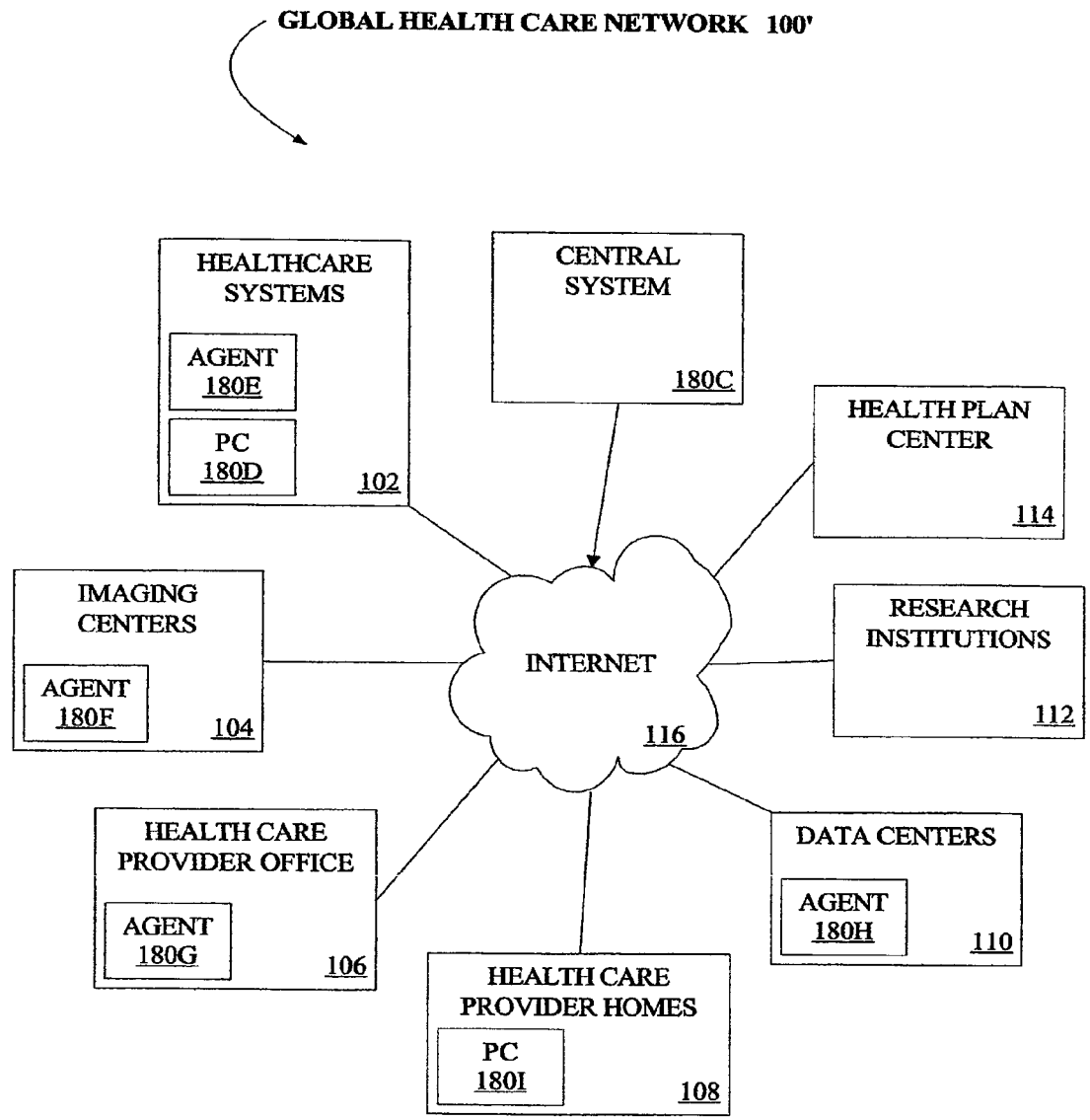
FIG. 9 is a block diagram of the global health care system of FIG. 1 incorporating a central system and distributed agents in accordance with the present invention.

There has so far been shown a global health network (FIG. 1) including various components thereof in detail (FIGS. 2-4). In accordance with the present invention, a distributed, centrally-mediated network for facilitating secure peer-to-peer organization, management, and access to digital patient medical records has been illustrated as connected into selected participants of the global health care network (FIGS. 5-8). It will be understood that the network of the present invention has application to any healthcare provider that stores and/or shares data with other health-care providers. Thus, with reference now to FIG. 9, global health care network 100' is shown identical to global health care network 100 (FIG. 1) and incorporating network 180 of the present invention.

Network 100' is thus seen to include agents 180E, F, G, H and I in health care systems 102, imaging centers 104, health care providers offices 106, data centers 110 and health care providers homes 108, respectively. Central system 180C is shown connected to Internet 116. A PC 180D is situated in healthcare systems 102. It will be appreciated that network 100' shows a block-diagram representation of the network of the present invention, and it will be apparent that many different agent configurations are provided in many different manners in many different health-care provider environments. Factors determining agent configuration for each particular health care provider include, but are not limited to: the types of networks and network connections, types of firewalls, types of medical information systems at participant sites, quantities and sizes of expected data files, geographic location of relevant buildings and equipment and other factors that will be apparent to the reader.

Figure 10:
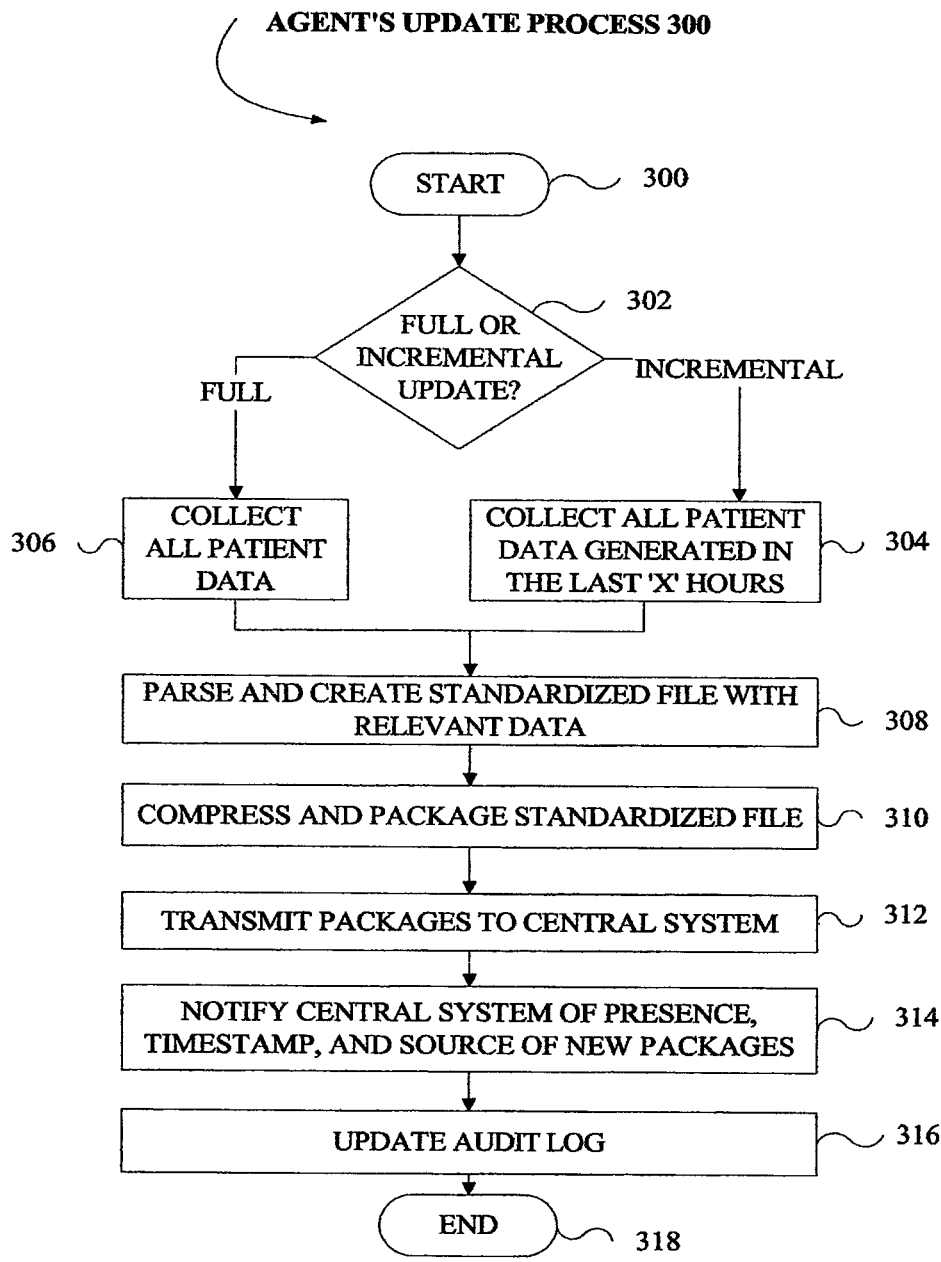
FIG. 10 is a flow chart showing a process by which an agent initiates a data review and update process.

With reference now to FIG. 10, an agent update process 300 is shown whereby each of the distributed agents described above identifies and processes newly created digital patient medical records, within a source distributed network participant (e.g. a healthcare system, imaging center, healthcare provider home, data center, etc.), to provide a metadata file for transmission to central server 180C. It is noted above that one or more agents are resident in each health care participant of the distributed network of the present invention.

At the start (step 300), it is first determined (step 302) if a particular update is an incremental update, performed once or multiple times per day, or a full update as may be performed upon the initial installation of a distributed agent into a new hospital or whenever it is otherwise desired to completely review all stored patient data. In the event of an incremental update, all patient data generated within the previous X (where "X" is some range of time typically from 0 to 24) hours is collected from the source hospital systems (step 304). Incremental updates are set to occur at customized and specific times and look back at records spanning a specific range of hours. Incremental update parameters are optimized based upon the characteristics of a particular hospital so as to minimize the impact of the software on the hospital information infrastructure. In the event of a full update, all patient data currently resident in the source hospital is collected (step 306). As noted above, patient data is collected using various software brokers designed to either query data from a particular medical information system (a 'pull') or to receive data from a medical information system programmed to 'push' or transmit data to the agent. The data collected from the hospital may take the form of data files transferred between systems or simply a stream of data (e.g. packets, frames, and/or cells depending on the underlying network technology) flowing through an established network interface (e.g. over TCP port 104, the standard DICOM interface to a PACS).

As each patient data stream or file is collected, it is parsed to identify its contents, selected contents being used to generate a patient metadata file (step 308), i.e. the various entries that will populate the database 187 of central system 180C, e.g. tables 191 through 197 shown in FIGS. 6A through 6G. In addition, data originating from systems that do not support ad hoc queries via a standard query language (e.g. many legacy radiology information systems which possess only HL7 interfaces) and which had been pushed to local database 224 (shown in FIG. 8A) for storage are parsed to find relevant patient data (e.g. radiology reports) with such data included in the metadata file. To parse a patient data stream or file, the format of the data is determined based on the originating device and the standard interfaces that the originating device supports (e.g. DICOM in the case of a PACS). Once the data file format is known, the contents and location of incoming information is known and selected information can be parsed out of the originating stream or and stored in the metadata file.

With reference to FIG. 10A, an excerpt from an exemplary metadata file 320 is shown demonstrating the parsed and aggregated metadata regarding a single imaging study for a particular patient. It is thus seen that the metadata file contains patient information that is descriptive of the various originating data file or stream formats from which that information was parsed in the manner described above. The metadata file described herein is in extensible Markup Language (XML), a language well-known and suited for this type of file.

Newly created metadata files are compressed, using a conventional data compression algorithm to decrease file size, and packaged into a single file for transmission (step 310). The packaged metadata files are transmitted over the appropriate secure network(s) to central system 180C (step 312). The agent then sends central system 180C an indication of the presence, time and date, and source of newly transmitted patient metafile packages (step 314).

The agent updates an internal audit log (step 316) to reflect the recently completed update, and the process ends (step 318).

Figure 11:
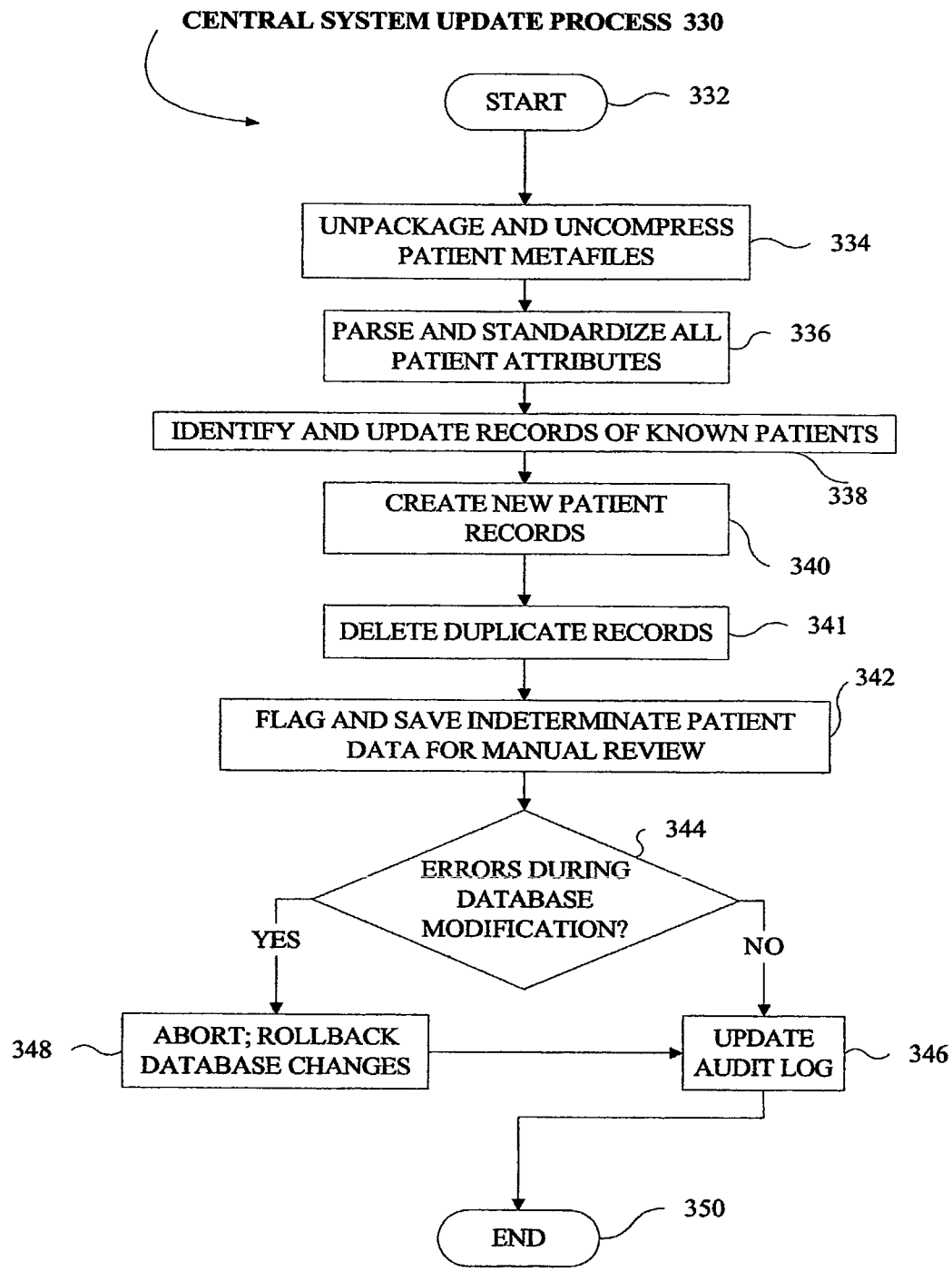
FIG. 11 is a flow chart showing a process by which a central server updates a database.

With reference now to FIG. 11, a central system update process 330 is shown wherein the central system 180C receives and processes packaged, metadata files transmitted by distributed agents to populate the index database tables described in FIGS. 6A-G.

At the start (step 332) of the process, newly received metadata file packages transmitted by distributed agents to the central system 180C are unpackaged by the central system from a single archive file into multiple files, and uncompressed into their original format (step 334). Data from the agent metadata file is parsed such that patient attributes are extracted and stored on the central system patient records (step 336). It will be appreciated that, while the above-described metadata file represents one exemplary distributed metadata file type, numerous formats of metadata files may exist depending on the type of patient data processed by a particular agent. As the central system receives agent files, patient attributes are thus identified, standardized for content and inserted into the central system database tables, exemplary ones of which are described with respect to FIGS. 6A-6G above.

Continuing with respect to FIG. 11, in a manner described in further detail in FIG. 11A below, update data relating to existing or known patients is identified and stored (step 338), data relating to new patients (i.e. those patients who are previously unknown to the central system 180C) is identified and stored (step 340) and duplicate data for known patients is deleted rather than stored (step 341). Data pertaining to patients whose status as new or known cannot be readily determined by computerized processing, is flagged for a manual review and determination by a human reviewer (step 342).

If there were no errors during the central system update process (step 344), the local audit log is updated to show the recently completed processing (step 346) and this process ends (step 350). If errors occurred during this update process, it is aborted and any database changes are rolled back to remove those changes from the database (step 348) and such errors are noted in the audit log (step 346) prior to the end of the process (step 350).

Figure 11A:
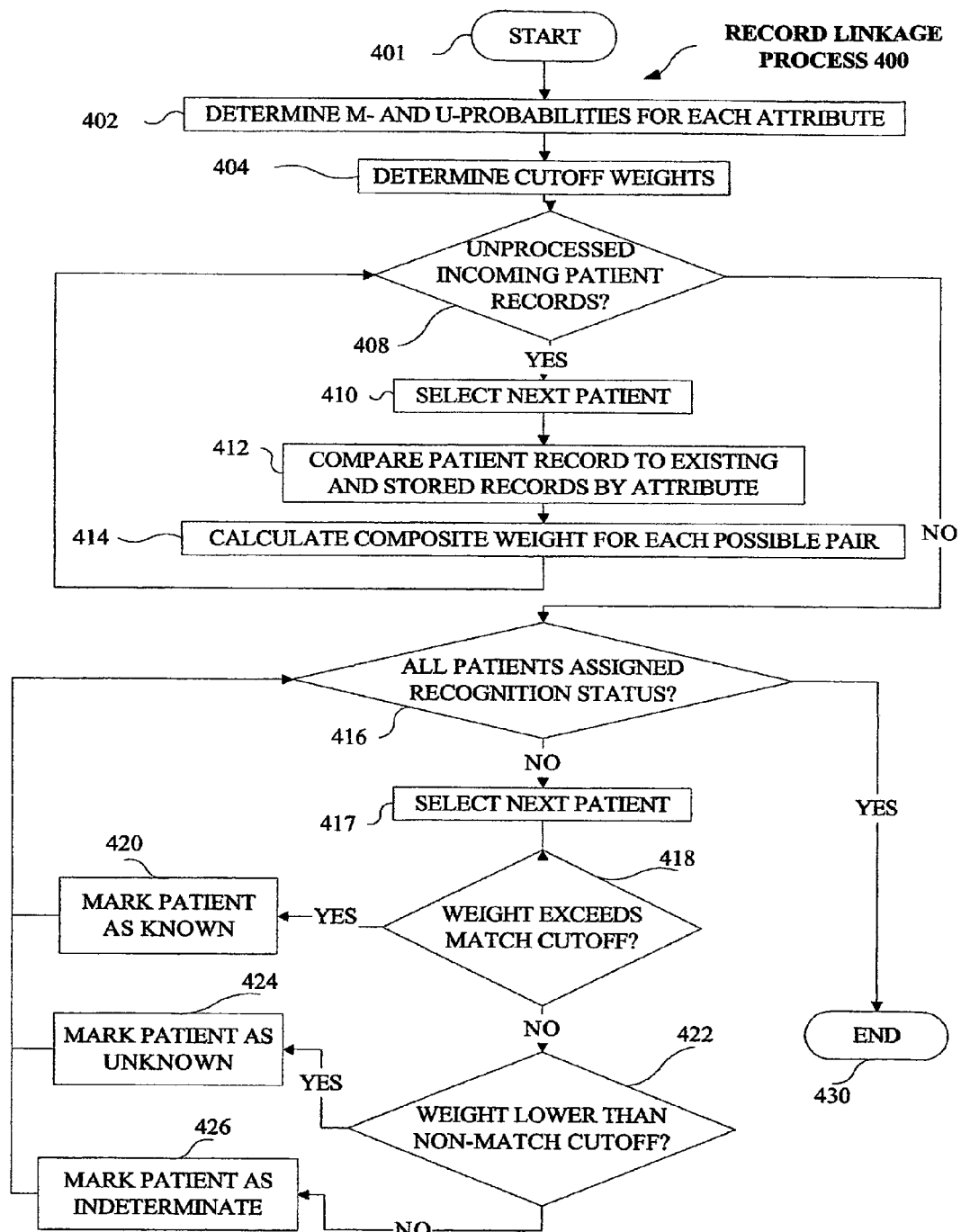
FIG. 11A is a flow chart showing a process by which a central server parses and standardizes patient attributes in accordance with FIG. 11 and categorizes patients as known, unknown, or indeterminate.

With reference now to FIG. 11A, there is shown a record linkage process 400 for processing newly received patient data metafiles from distributed agents by central system 180C to determine the identity of each patient relative the list of patients known to date by central system 180C in the absence of a unique patient identifier as is the case in sharing data between multiple medical institutions. The invention attempts to automatically link patient records in the absence of a unique patient identifier, for example in the absence of a unique and discrete patient name, across different healthcare providers. As such, process 400 assigns a recognition status to each incoming patient record based upon the available data to determine if the patient already has some data stored in the database 186 of central system 180C (i.e. is a known patient), is unknown to the system (i.e. a new patient), or is indeterminate (there insufficient data available to make the known/unknown determination in an automated fashion and manual intervention is required).

At the start (step 401) the "M" and "U" probabilities are determined for each patient attribute (step 402) where the attributes are the demographic data or components of data such as shown in tables 191 through 194 of FIGS. 6A through 6D. As is understood in the art, M indicates the probability that a comparison of a particular attribute's values agrees if a pair of records identify the same individual and U indicates the probability that a comparison of a particular attribute's values agrees if a pair of records do not identify same individual, where M and U are then used to calculate a "binit" agreement weight (the base 2 logarithm of M divided by U) and disagreement weight (the base 2 logarithm of I-M divided by 1-U). In the described embodiment, M and U are estimated prior to processing any patient records based on the "Expectation Maximization" algorithm (see e.g. Winkler, W. E. 1994 Advanced Methods of Record Linkage. American Statistical Association, Proceedings of the Section of Survey Research Methods, 467-472) applied to a large sampling of known patient records and attributes. In alternate embodiments, well known to those skilled in the art of probabilistic record linkage, M and U can be estimated 'on the fly' as real patient meta-data is processed and analyzed.

After determining M and U probabilities for each attribute, cutoff scores are determined (step 404) by which recognition status can later be assigned to each patient record. Known patients will have a score above the 'match' cutoff score and unknown patients will have a score below the 'non-match' cutoff score. As described below, patient records falling between the predetermined cutoff scores are identified as indeterminate. In the described embodiment, these cut-off scores have been calculated in advance of record processing through the offline analysis of a large, representative sample of patients where a unique identifier exists that can serve as a benchmark by which to judge the accuracy of the chosen cut-off weights. In alternate embodiments, such cut-off scores may be estimated 'on the fly' as patient meta-data is being analyzed by the central system 180C.

Once the M probabilities, U probabilities, agreement/disagreement weights, and cutoff scores have been determined, it is assumed that all incoming patient records originate from patients whose recognition status (i.e. known vs. unknown vs. undetermined) is undetermined. For each unprocessed incoming patient record (steps 408, 410), each demographic attribute of this incoming metadata file record is compared pair-by-pair with the corresponding attribute in all known patient records existing and stored within the database 187 of central system 180C (step 412). For each such patient record by patient record comparison, the agreement/disagreement weights for each attribute are summed to produce a composite score for a particular patient record pair (step 414). Individual weights may be frequency adjusted prior to the creation of the composite score to account for additional discriminating power of certain attributes (e.g. a less common surname such as 'Menschik' has far more discriminating power than does the more common 'Smith').

Once the composite scores have been calculated for all possible pairs, the score of each possible pair (steps 416, 417) is compared to the cutoffs to determine: 1) if the composite score exceeds the predetermined match cutoff score (step 418), the patient record is identified as for an existing or known patient (step 420), 2) if the composite weight is less than the predetermined non-match cutoff (step 422), then the patient record is identified as for a new patient (step 424) and 3) if the composite weight falls between the match and non-match cut-off weights then the patient record is identified as for an indeterminate patient (step 426). Once the recognition status of each incoming patient record is so determined, the process ends (step 430).

While the invention has application to many different health-care providers in many different environments and configurations, for purposes of explanation system users will generally be considered to be physicians. Network participants, including source participants where large quantities of digital patient medical records are generated and/or are stored, will be described as hospitals or imaging centers. Thus, the described processes are exemplified in the form of a physician finding and viewing or having transferred for local use, digital patient medical records, including diagnostic images, stored at remote hospitals or imaging centers.

Due to the sensitive nature of patient medical data, it is important that only appropriate users can obtain access to the patient medical records stored on central system 180C, and subsequently to obtain the digital patient medical records from the source. Secure access requires both authentication of the user so that the system recognizes and tracks that user, as well as authorization of that user to access particular data. The exemplary method for authenticating users of the system is to require pre-registration of all users who are identified by digital authentication tokens upon login to the system. Such a process is described with respect to user registration process 450 of FIG. 12.

At the start of the process, it is determined if a user requesting access to central system 180C has an appropriate digital authentication token (step 454). It will be understood that such a digital authentication token indicates that a user has been granted at least initial access to the system. Various types of digital authentication tokens and processing methods are known in the art.

If the user has no authentication token, an authentication token is created or otherwise obtained for that user (step 456) and transmitted to the user (step 458), typically by a secure communication whether digitally or "out-of-band."

Upon the receipt of a valid user authentication token (step 459), user demographic data is extracted from the token (step 460) and an input registration form is displayed for completion by the user (step 462).

User data is collected (step 464) and evaluated to determine if a user should be registered for access to central system 180C. It will be understood that the collected user data is sufficient to determine the appropriate level of access control for a user (e.g. search capability by physicians, updating institutional information by hospital administrators, etc.). Note that authentication of the user alone is insufficient to grant access to patient medical data. Some authenticated users (e.g. physicians) are able to search the data stored on the central system 180C, but access to actual patient medical records requires a specific authorization as described below.

Upon evaluating the user data and validating that the user should receive access to central system 180C, a user account is created on central system 180C (step 466) and the user registration process terminates (step 468).

Figure 12:
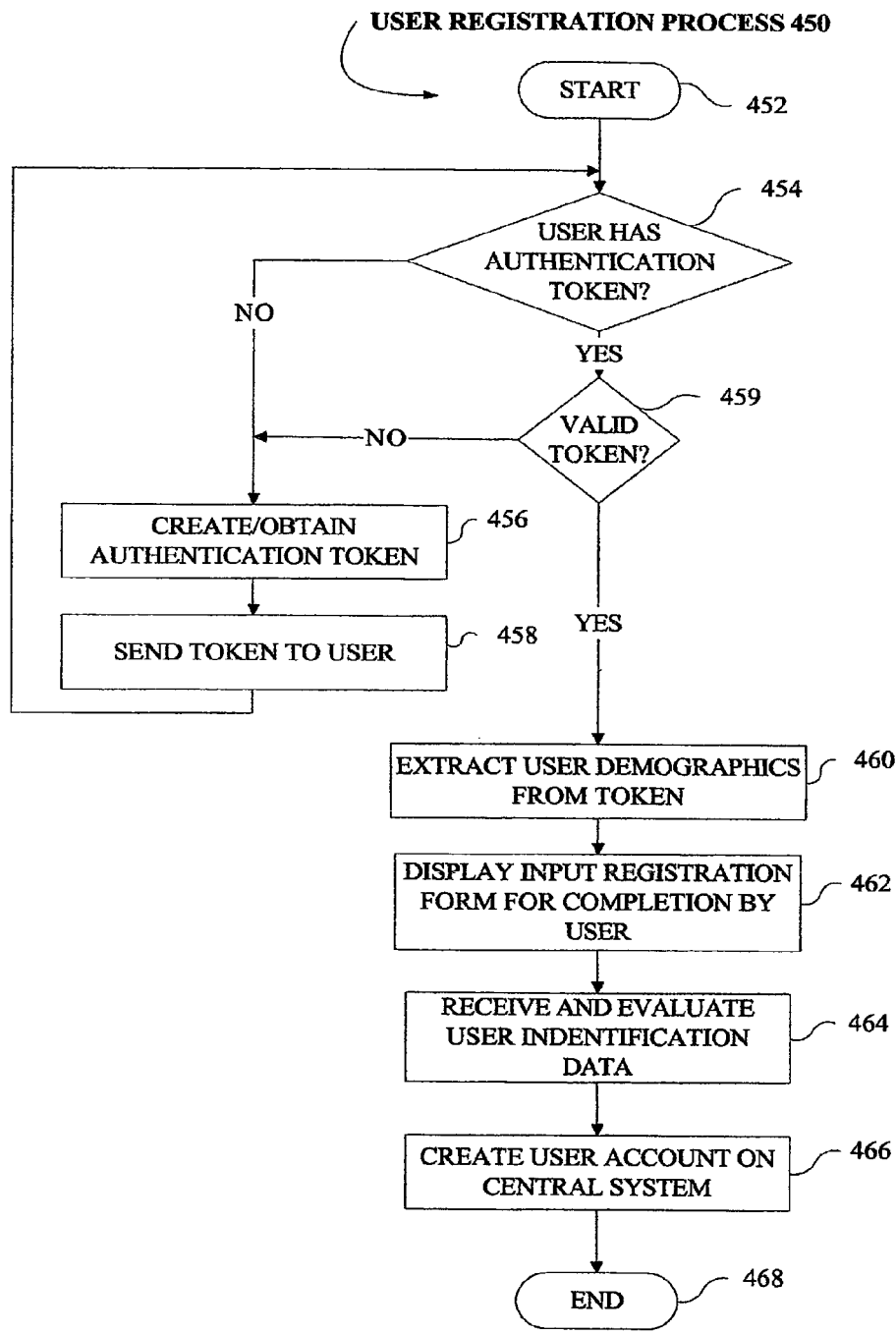
FIG. 12 is a flow chart showing a process by which a new user is registered to use the present system.
Figure 13:
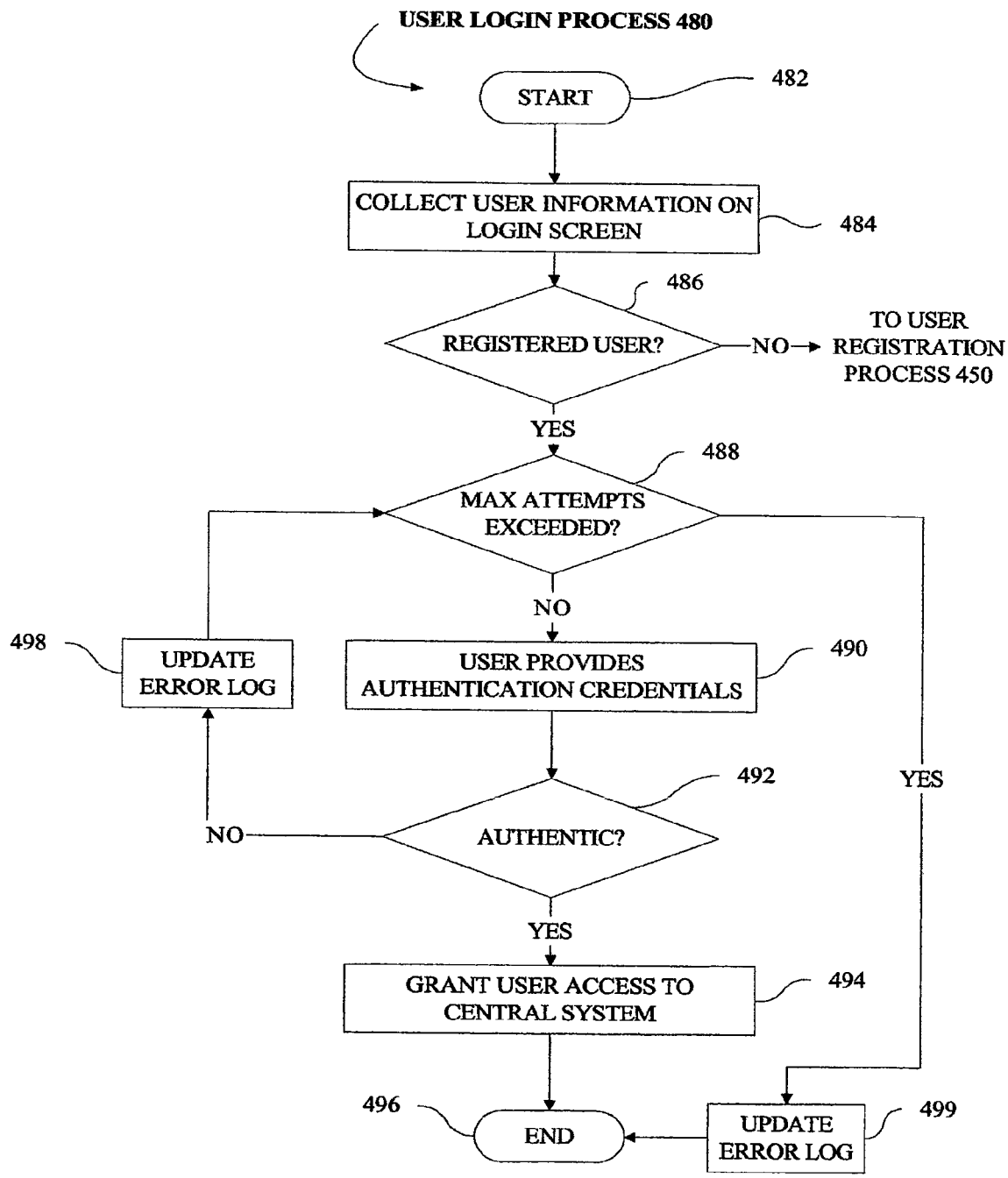
FIG. 13 is a flow chart showing a process by which a registered user logs in to use the present system.

As noted above, it is important to provide for the security of the overall system so as to insure the security of patient medical data. With reference now to FIG. 13, there is shown a user login process 480 whereby a registered user can gain access to his permitted files and capabilities on central system 180C. At the start of the process (step 482), a login screen is displayed or transmitted by central system 180C to a user desiring access to the central system. User-supplied information is collected through the log-in screen (step 484) to determine if the particular user is a registered user (step 486). If the particular user is not a registered user, that unregistered user is directed to the user registration process 450 (FIG. 12).

If the user information collected indicates a registered user and that registered user has not exceeded a preset number of maximum attempts to provide authentication credentials (step 488), the authentication credentials, for example a password, is provided by the user and collected by the central system (step 490). If the authentication credentials identify the user as known to the system (step 492), then the user is granted access to his permitted files and activities on the central system (step 494), for example through a web page user interface which may be customized for the particular authenticated user. The process would then end (step 496).

If the user does not provide the information necessary for authentication (step 492), then an error log tracking failed login attempts is updated (step 498) and, if a maximum number of failed login attempts is exceeded (step 488), then an error log is again updated (step 499) indicating the maximum number of authentication attempts has been exceeded. Users exceeding the maximum number of allowed login authentication attempts will be subject to increased security measures, for example requiring re-registering and/or the obtaining of a new password or other authentication credentials.

Figure 14:
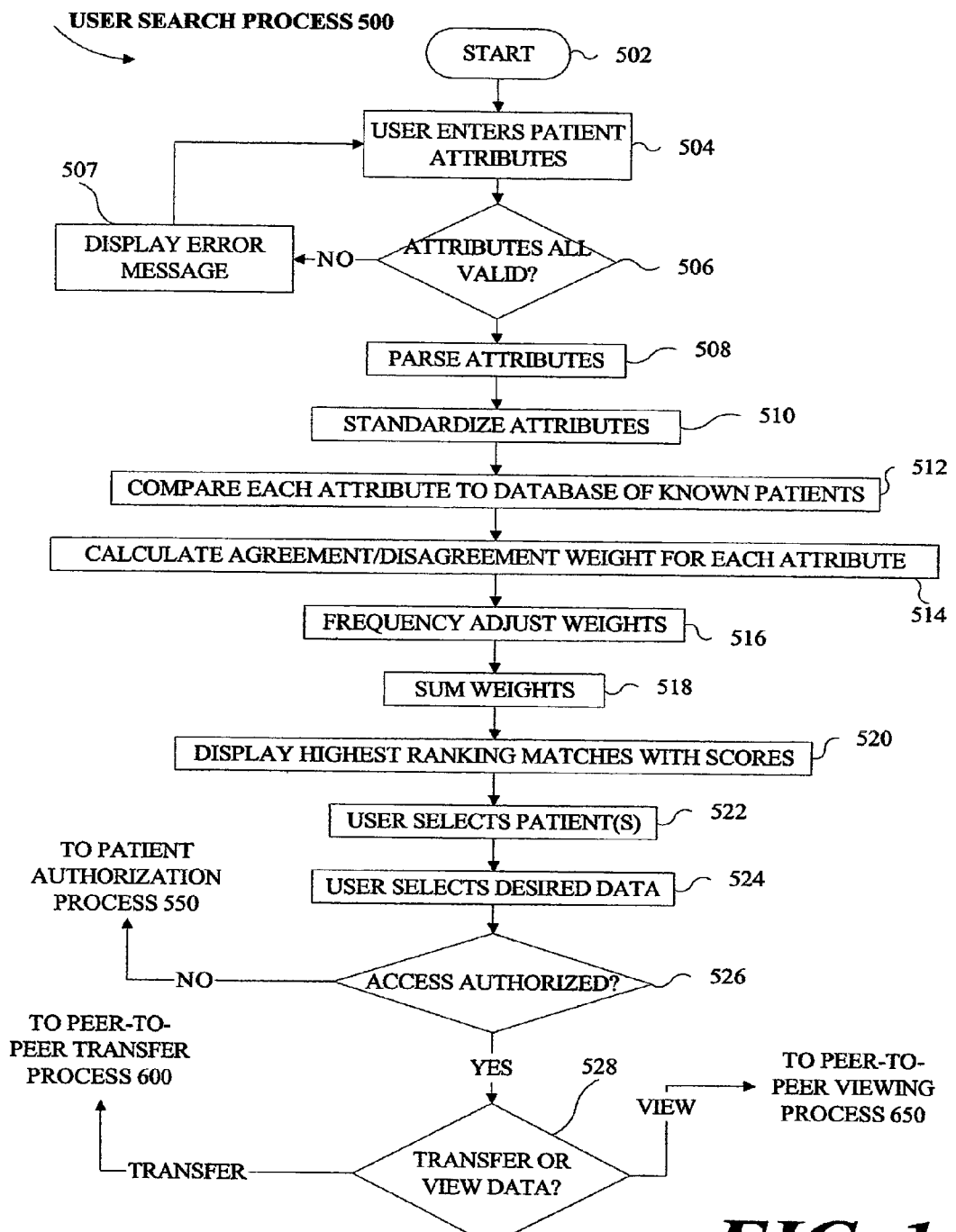
FIG. 14 is a flow chart showing a process by which a user search is performed to find desired patient medical data.

With reference now to FIG. 14, a user search process 500 is shown whereby an authenticated user who is permitted to search patient meta-data for a particular patient, such as a physician, may search central system 180C to find desired patient records. As described, such patient records stored on central system 180C function as pointers to identify the remote digital patient medical data stored in the source hospitals.

To initiate the process (step 502), a user enters patient attributes describing the patient whose data the user wishes to access (step 504). Exemplary patient attributes include but are not limited to: name, address information, age, gender and other identifying information. The system checks to see that all attributes are valid (step 506) and, if invalid attributes are found, will display an error message (step 507) requesting reentry of the invalid patient attribute data. Invalid attribute data may comprise, for example and without limitation: a patient name including numbers, a patient address with an incorrectly indicated state identifier, and other information where the user-supplied attribute is not in accord with possible attribute data.

If the user-entered patient attribute data is valid (step 506), the patient attributes are parsed into discrete entries (step 508) and standardized in accordance with standardization guidelines built into the system. Address information, for example, may be standardized into discrete standardized address fields, patient names including prefixes, titles and suffices into standardized patient name fields, etc.

Each standardized patient attribute is then compared to the attributes of known patient records stored in central system 180C (step 512), i.e. those attributes stored in the data files described with respect to FIGS. 6A-6G. Using the M and U probabilities described above and illustrated as step 402 of FIG. 11A, agreement and disagreement weights are determined for each attribute again in accordance with the known art of probabilistic record linkage (step 514), the weights then being adjusted for frequency (step 516) (again, e.g. a match on a rare surname such as "Menschik" having a higher discriminating power than a match on "Smith") and summed (step 518). A listing of potentially matching patient records is identified and displayed in rank order from likeliest to least likely match (step 520).

Figure 15:
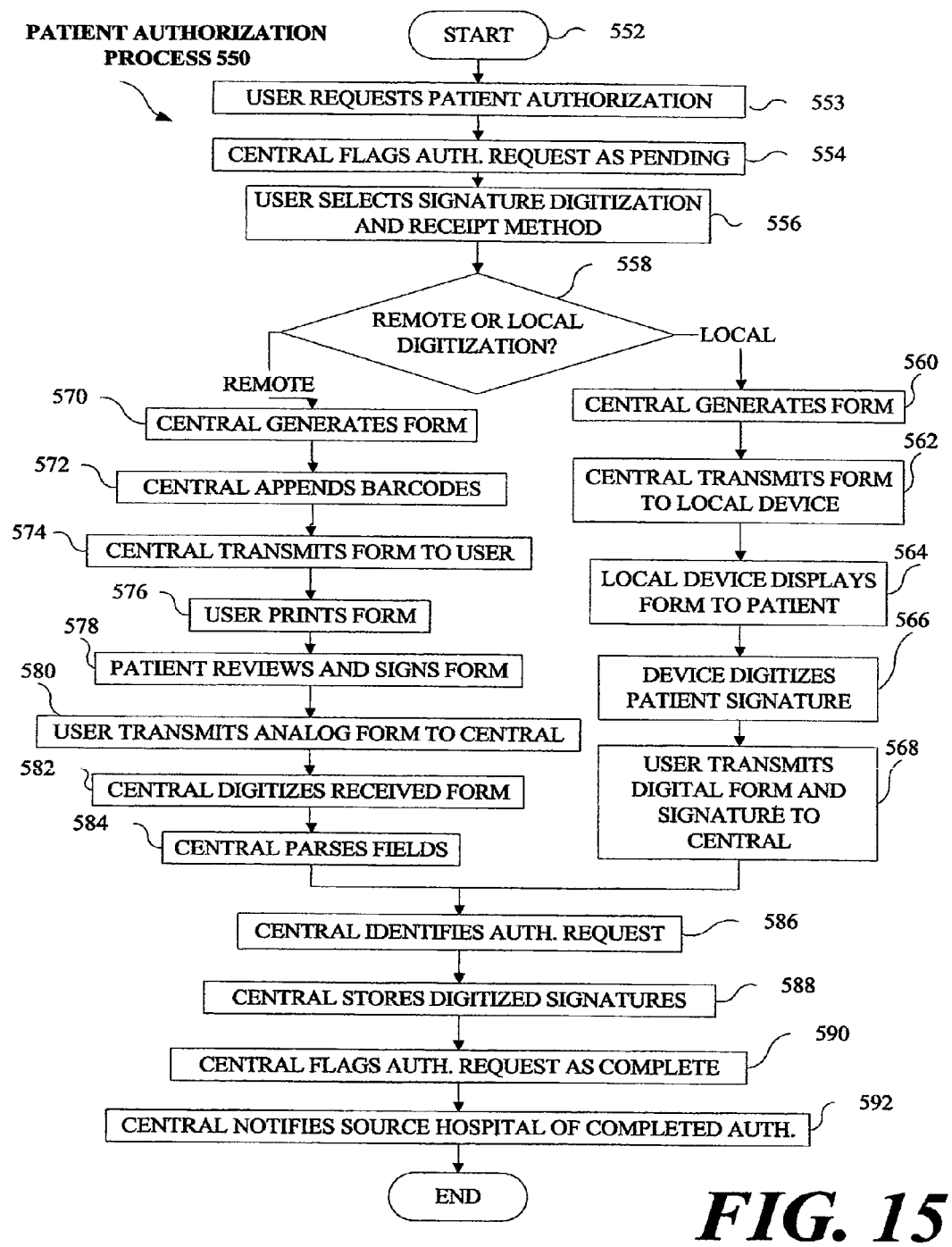
FIG. 15 is a flow chart showing a process by which a patient digitally authorizes access to his or her medical data.

If the user finds a match with the desired patient (step 522) he can then select that component of the patient's medical record in which he is interested (step 524). The central system then checks its authorization database to determine if this particular user has a valid authorization from the patient to access this specific data (step 526). If no valid patient authorization exists granting the user access to the data (step 526), then patient authorization process 550 is initiated (FIG. 15). If a valid patient authorization exists granting the user access to the desired patient data, (step 526), then the user selects whether he wishes to view that data or have that data transferred to him locally (step 528). The peer-to-peer viewing process is described with respect to FIG. 17 below, while the peer-to-peer data transfer process is described with respect to FIG. 16 below.

As noted above, patient medical information is highly sensitive and the privacy of such information must be protected under national and international data privacy laws and regulations. Patient medical information is made available only to those parties, such as the patient's physicians, who are authorized by the patient to access it. With respect now to FIG. 15, a patient authorization process 550 is shown whereby, using a digital process, a patient (where it is understood that "patient" also refers to authorized proxies and surrogates for a patient, e.g. the parent of a minor) expressly authorizes by signature the release of particular medical data to a particular party.

As described with respect to FIG. 13 above, the patient authorization process typically will occur following the successful identification of patient digital patient medical data by a system user. That is, the user has successfully searched central system 180C finding a patient record stored on the central system 'pointing to' or identifying the larger complete digital patient medical data contained at the source hospital. Once found, the system user cannot gain access to the patient data unless the patient has authorized that access (see FIG. 14, step 524). At the start of the authorization process (step 552), the system user requests patient authorization for the release of specified data (step 553) and central system 180C flags that authorization request as pending (step 554).

Once the authorization request is established, the user selects a method by which a patient signature is to be digitized and received by the central system, indicating patient authorization for release of the identified data to the system user (step 556). In the illustrated embodiment, two methods of signature digitization and receipt are described. In the first method, termed the "local" method, a patient signature is digitized directly on a transduction device (e.g. a personal digital assistant, a pen-sensitive computer monitor, etc.) and communicated to the central system, while in the second method, termed the "remote" method, the patient signature is written on paper, transmitted to a central system operator where it is digitized upon receipt (e.g. automatically by a digital facsimile receiver, manually by a scanner, etc.). Both methods represent rapid and efficient means of obtaining a digital form of patient authorization.

Considering first the local method of patient authorization (step 558), the authorization process is completed on a transduction device including an input device for receiving a handwritten signature and directly converting that signature into a digitized, stored signature file. Many such computer devices are known in the art, including but not limited to: an electronic 'tablet,' a touch-sensitive computer monitor screen and one of many personal digital assistants (PDAs) such as the well-known Palm™ and Compaq IPAQ™ devices having touch-sensitive screens.

Upon the selection of the local signature mode, the central system 180C retrieves and/or generates all of the patient authorization forms required by and specific to the particular source hospital possessing the desired digital patient medical data (step 560). As is described above, central system 180C stores only an index pointing to the remotely located digital patient medical data, the medical data itself remaining in the possession of the source entity, i.e. the hospital, doctor's office, radiology practice or other medical care provider who generated the medical data or otherwise came into possession of the medical data.

It will be understood that different medical service providers have different forms and formats for patient authorizations. Each time a new health care provider participates in the system of the present invention, their authorization forms are collected and stored on central server 180C for later use in template form with empty fields (such as patient name) to be filled in dynamically when needed. It will be further understood that even when the patient signature is provided on the transduction device, the authorization form may be printed and provided to the patient for review.

Subsequent to the generation of the patient authorization limns (step 560), the central system transmits those forms (step 562) to the selected local device for display to (step 564) and approval by the patient. The patient reviews the authorization forms and indicates his or her approval by signing the forms on the local device such that the signature is directly digitized by and stored on the device (step 566). The digitized signature with the completed authorization forms is transmitted back to the central system (step 568).

Describing now the process by which a remote patient authorization signature is provided (step 558), in a manner similar to that discussed above, central server 180C selects and/or generates the necessary patient authorization forms (step 570) with appropriate codes such as barcodes (step 572) by which the subsequently returned forms and their data fields can be identified. The central server transmits the forms (step 574) to the user, typically by transmitting the forms electronically (e.g. displaying them on the screen of a web browser, sending them via facsimile, etc.). The user prints the forms (step 576) for review and signature by the patient (step 578).

The signed forms are then transmitted by the user, in the signed, paper format, back to the central server (step 580), for example by facsimile from a doctor's office. The forms and their data fields received by the central server are identified based on the barcodes, digitized (step 582) automatically by the receiving device (e.g. by facsimile software running on the central server) or manually (e.g. by a conventional scanner) and the digitized data is parsed into fields (step 584) for electronic processing and storage.

It will be appreciated that at this point central system 180C contains both the authorization form(s) and signature in digital format. The central system identifies the authorization request based on which the forms were generated and signed (step 586), for example using the barcode markings in the remote process and digital information in the local process, and stores the authorization signature in digital format (step 588). Central system 180C places an indicator in an appropriate data file, i.e. the appropriate fields in table 197 of FIG. 6G, indicating the authorization request has been approved and the signature received (step 590). The central system then notifies the source hospital that patient authorization has been received to release the patient medical data to the user, typically electronically.

It will be understood that, as described above, a physician has searched the patient records contained on central server 180C to identify that desired digital patient medical information in fact exists at a hospital participating on network 180. The physician has obtained from the patient an authorization for the source hospital to make that patient data available to the user. The source hospital has received notice of the patient authorization to release the specified patient data. It is now appropriate for the patient data to be released by the source participant for review by the physician. This can occur in one of at least two ways, both of which are "peer-to-peer" in their direct connection between the involved parties, avoiding the transfer of data to or through the central system 180C further ensuring patient privacy and avoiding data bottlenecks on the network. In accordance with a first process described with respect to FIG. 16, the data is transferred in a peer-to-peer manner from a source institution to a destination institution. In a second process described with respect to FIG. 17, the user views the data directly from the source.

It will be understood that, as used herein, the term 'direct' when used to describe a data transfer means that no data passes through the central server. All data is 'directly' transmitted from the source agent to the recipient agent or other specified device. Data will pass through a network or combination of private and public networks which may include the Internet.

Figure 16:
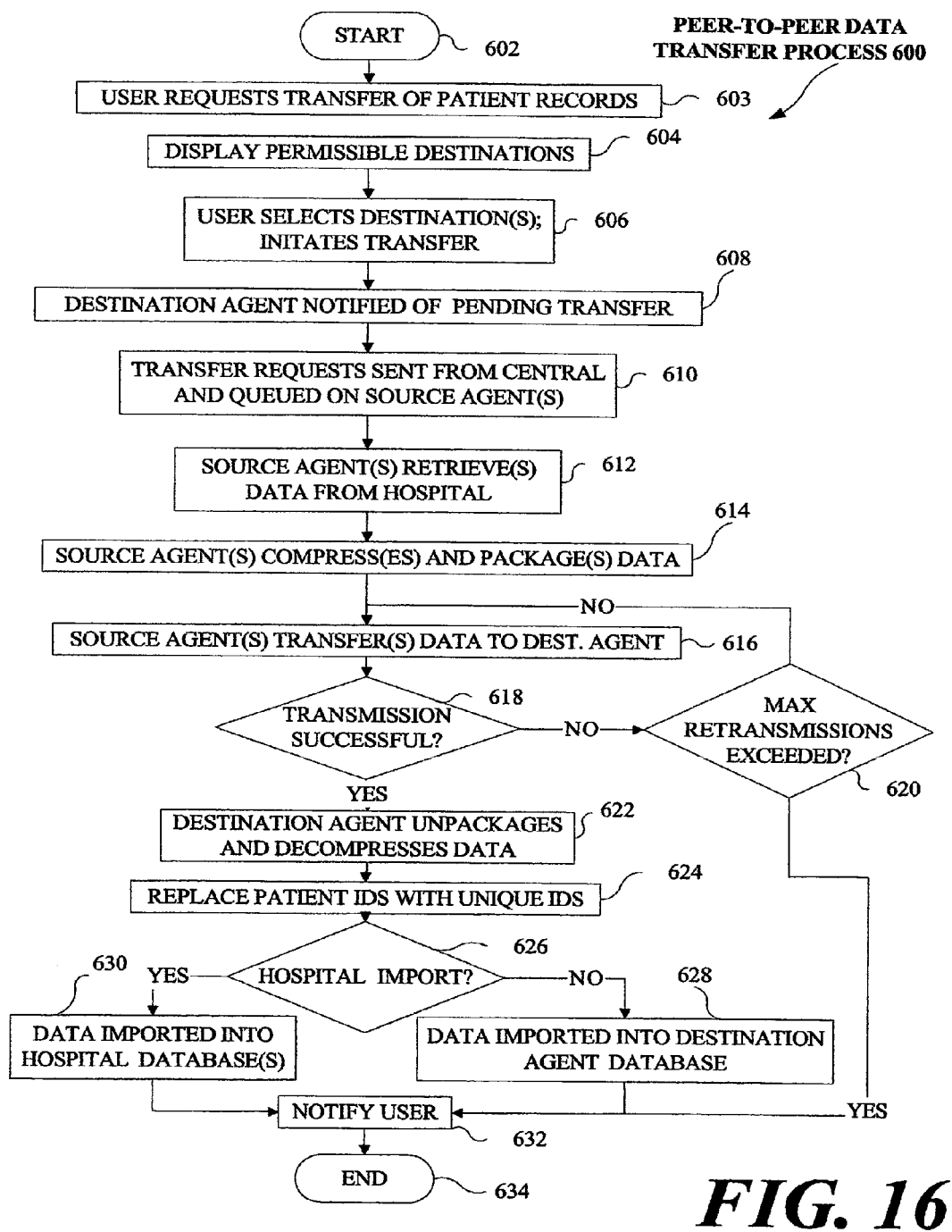
FIG. 16 is a flow chart showing a-process by which a peer-to-peer data transfer occurs.

With reference now to FIG. 16, at the start (step 602) of a data transfer, an authenticated user who is logged on to central system 180C, who has selected specific patient records following a successful search, and who is authorized by the patient to access such records, requests the transfer of the selected patient data (step 603) found in the earlier-completed search of the central system patient records. Based on factors including the location of the system user, the user's privileges at particular institutions, and the contents of the patient authorization, the central system displays a list of permissible destinations for the patient data (step 604). The user then selects one of the permissible destinations to initiate a transfer (step 606).

Central system 180C notifies the agent at the selected destination to expect the data transfer (step 608) and the central system then transmits the transfer request to the agent associated with the data source (step 610) where it is queued for processing. If the requested patient data is available from multiple sources, the transfer request may be sent to the agents associated with each of those sources.

Upon receipt of the data transfer request, the source agent(s) retrieves the specified patient data from the storage location within the source (i.e. hospital) (step 612) either using the broker software specific to the storage location, or directly from database 224 when the source location does not support ad hoc queries. The data is compressed and packaged (step 614) for electronic transmission to the identified destination agent (step 616). Transmission to the destination agents occurs over the IPSec-secured network links between the two agents and standard protocols are used to determine a successful transmission (step 618). Transmission may be repeated up to a predetermined maximum number of times (step 620) to facilitate a successful transmission.

Upon successful receipt of the patient data transmission, the receiving destination agent unpacks and decompresses the patient data (step 622), replacing the existing patient identifiers with patient identifiers unique to the new data location (e.g. pre-pending an alpha-numeric code to identify the original source institution and avoid data collision if imported into the destination institution's systems). The data is stored either in a selected recipient hospital database (steps 626, 630) or within the destination agent database (steps 626, 628) depending on the pre-determined settings as desired by the destination institution upon the installation of their agent. The user is notified that the requested data has been successfully received and is available for viewing (step 632) and the process ends.

It will be appreciated that many different options are now available by which the user can view the patient data, for example a local, high-resolution monitor. It will also be appreciated that the newly stored digital patient medical data will, upon the next distributed agent and central system update process (described with respect to FIGS. 10 and 11 above) be indexed within the central system for potential finding and use by another user.

Figure 17:
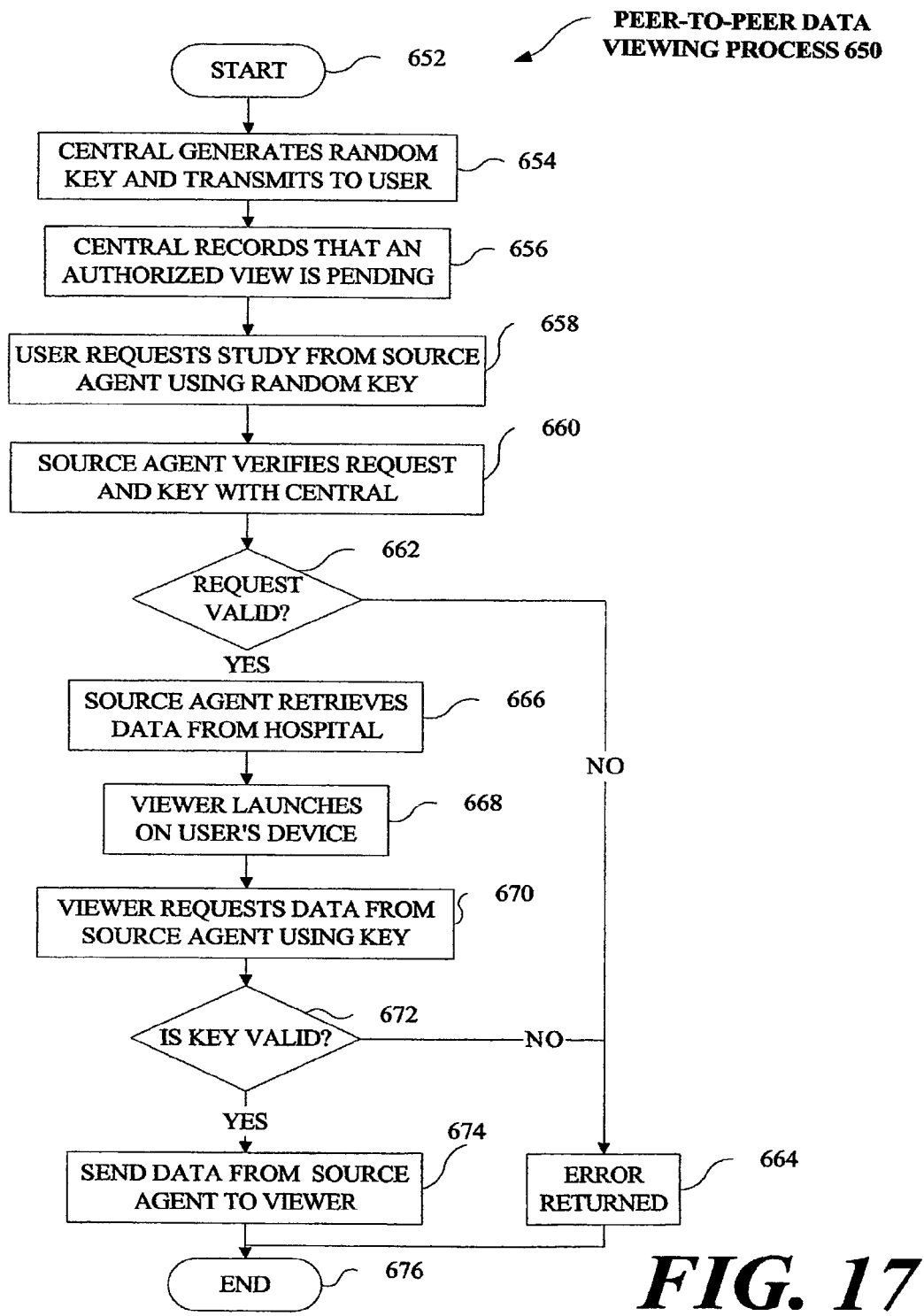
FIG. 17 is a flow chart showing a process by which a peer-to-peer data viewing process occurs.

As noted above, alternatively to transferring the desired patient data to the user, that data may be made available for viewing using the peer-to-peer viewing process 650 described with respect to FIG. 17.

At the outset of the viewing process (step 652), the central server generates a random security key, transmits that key to the user (step 654) and flags in a database such as the appropriate fields of the table in FIG. 6G that a user view of the particular digital patient medical data has been authorized and is pending (step 656). Subsequently, the user requests the desired data directly from the source agent serving the source hospital here the desired patient data is stored. Requested access to the patient data includes the use of the above-provided security key (step 658). Such requests will typically be automatic as in the case of an automated re-direction of a user web-browser from the central web server 182 to the reverse proxy server on the source agent front-end 180A-1.

The source agent transmits the security key to the central system to receive verification that the key is valid and the requested digital patient medical data should be made available for viewing (step 660). If the central system returns an error indicating the security request is invalid (steps 662 and 664) the process terminates (step 676) without the patient data being provided for viewing.

If the central system indicates the user request and security key are valid (step 662) then the source agent retrieves the data from its storage location in the source hospital (step 666) and a viewer, for example an application integrated with an Internet browser, is launched on the user's computer (step 668). The viewer, using the security key on the user's computer, transmits a request to the source agent to load the data (step 670). The source agent checks the second-submitted key against the security key previously validated by the central server (step 672) and if the security keys match, transmits the patient data for viewing on the user computer's viewer (step 674).

There has thus been provided a distributed network including distributed agents communicating with a central system for mediating secure, peer-to-peer transfers of digital patient medical data between healthcare providers that is scalable to arbitrary numbers of participating institutions and users, which can identify patients across multiple institutions in the absence of a unique patient identifier system shared by such institutions, which integrates with any medical information system in use at participating institutions, which conforms to international standards for the privacy and security of patient data, and which allows users at non-digital institutions to access data from other digital entities.

As described above, the distributed agents collect and summarize information relating to patient medical data, generated and/or stored in medical information systems at local hospitals and other health-care providers, into a metadata file. The collected data is transmitted by the distributed agents, in the form of the metadata files, to the central system, where it is parsed, formed into database entries and stored in a patient-centric fashion. Subsequently, authenticated users, such as physicians, can search the central server data to find pointers to the original medical data, obtain the authorization of patients to access particular records, and view or receive the original digital patient medical data directly from the source institution storing such records.

The system thus enables the organization, finding and access to digital patient medical information that is typically unavailable due to physical, electronic, political, and/or legal barriers between medical institutions and healthcare providers and which is typically partitioned among multiple information systems within a single medical institution, often in a proprietary format. Moreover, patients themselves serve as the gatekeepers to their data in line with the requirements of international data privacy laws and regulations. It enables the sharing of disperse, varied-format patient medical data records in near-real time while maintaining the privacy of the patient and the security of the medical information.

The present invention has application in the healthcare industry and particularly amongst distributed health-care providers desiring to access digital medical patient data for the benefit of the patient and treating physician.

The invention as described is not thus limited. There will now be apparent changes, variations, improvements and updates that fall within the spirit and scope of the invention.

What is claimed:

1. A method for managing distributed medical data, comprising the steps of:
   providing a plurality of software brokers in communication with a plurality of patient medical files in a medical information system, each respective software broker generating metadata files for locally stored patient medical files; and
   each said software broker performing the steps of:
   identifying, periodically on a programmed basis, patient medical files each containing digital medical data relating to a patient;
   creating, for each of the identified patient medical files, a metadata file containing attributes relating to the contents of the identified patient medical file and the storage location of the identified patient medical file, wherein creating said metadata file comprises parsing each of the identified patient medical files to extract said attributes relating to the contents and storage location of the identified patient medical file, standardizing a meaning and format of the attributes whereby the same attributes represent data having the same meaning and format across different medical information systems, and storing the standardized attributes in the metadata file;
   packaging each of the metadata files for transmission to a remote central computer; and
   transmitting, in a secure manner, each of the metadata files to the remote central computer.

2. A method in accordance with claim 1 wherein the software broker retrieves data from the medical information system.

3. A method in accordance with claim 1 wherein the software broker receives data transmitted by the medical information system.

4. A method in accordance with claim 1 wherein the step of transmitting includes transmitting over a digital virtual private network.

5. A method in accordance with claim 1 wherein the transmitting step includes securely transmitting the metadata file to the central computer over a digital physical private network.

6. A method in accordance with claim 1 and further including the step of transmitting to the central computer a summary file identifying the plurality of metadata files.

7. A method in accordance with claim 1 wherein each of the metadata files further includes attributes relating to the identity of a patient.

8. A system for managing distributed medical data, comprising:
a plurality of software brokers in communication with a plurality of patient medical files in a medical information system, each respective software broker generating metadata files for locally stored patient medical files, each software broker comprising:
a processor;
a memory connected to the processor and storing instructions for controlling the operation of the processor;
the processor operative with the instructions in the memory to perform the steps of:
identifying, periodically on a programmed basis, patient medical files each containing digital medical data relating to a patient;
creating, for each of the identified patient medical files, a metadata file containing attributes relating to the contents of the identified patient medical file and the storage location of the identified patient medical file, wherein creating said metadata file comprises parsing each of the identified patient medical files to extract said attributes relating to the contents and storage location of the identified patient medical file, standardizing a meaning and format of the attributes whereby the same attributes represent data having the same meaning and format across different medical information systems, and storing the standardized attributes in the metadata file;
packaging each of the metadata files for transmission to a remote central computer; and
transmitting, in a secure manner, each of the metadata files to the remote central computer.

9. A system in accordance with claim 8 wherein the software broker retrieves data from the medical information system.

10. A system in accordance with claim 8 wherein the software broker receives data transmitted by the medical information system.

11. A system in accordance with claim 8 wherein the processor transmits the metadata files over a digital virtual private network.

12. A system in accordance with claim 8 wherein the processor securely transmits the metadata file to the central computer over a digital physical private network.

13. A system in accordance with claim 8 wherein the processor transmits to the central computer a summary file identifying the plurality of metadata files.

14. A system in accordance with claim 8 wherein each of the metadata files further includes attributes relating to the identity of a patient.

15. A system for managing distributed medical data, comprising:
a plurality of software brokers in communication with a plurality of patient medical files in a medical information system, each respective software broker generating metadata files for locally stored patient medical files, each software broker having a processor and a memory connected to the processor for storing instructions for controlling the operation of the processor, the instructions when processed by the processor implementing:
means for identifying, periodically on a programmed basis, patient medical files each containing digital medical data relating to a patient;
means for creating, for each of the identified patient medical files, a metadata file containing attributes relating to the contents of the identified patient medical file and the storage location of the identified patient medical file, wherein said creating means comprises parsing means for parsing each of the identified patient medical files to extract said attributes relating to the contents and storage location of the identified patient medical file, means for standardizing a meaning and format of the attributes whereby the same attributes represent data having the same meaning and format across different medical information systems, and means for storing the standardized attributes in the metadata file;
means for packaging each of the metadata files for transmission to a remote central computer; and
means for transmitting, in a secure manner, each of the metadata files to the remote central computer.

16. A nontransitory computer readable storage medium containing control instructions operative on a computer such that execution of said control instructions by said computer causes said computer to perform the steps of:
identifying, periodically on a programmed basis, locally stored patient medical files each containing digital medical data relating to a patient;
creating, for each of the identified patient medical files, a metadata file containing attributes relating to the contents of the identified patient medical file and the storage location of the identified patient medical file, wherein creating said metadata file comprises parsing each of the identified patient medical files to extract said attributes relating to the contents and storage location of the identified patient medical file, standardizing a meaning and format of the attributes whereby the same attributes represent data having the same meaning and format across different medical information systems, and storing the standardized attributes in the metadata file;
packaging each of the metadata files for transmission to a remote central computer; and
transmitting, in a secure manner, each of the metadata files to the remote central computer.

* * * * *